United States Patent
Hirota

(10) Patent No.: US 8,100,833 B2
(45) Date of Patent: Jan. 24, 2012

(54) DIAGNOSTIC IMAGING SYSTEM AND PROCESSING METHOD FOR PRODUCING REDUCED FRAME RATE IMAGES FROM DATA COLLECTED AT A HIGHER FRAME RATES

(75) Inventor: Kazuhiro Hirota, Kanagawa (JP)

(73) Assignee: Terumo Kabushiki Kaisha, Shibuya-Ku, Tokyo (JP)

( * ) Notice: Subject to any disclaimer, the term of this patent is extended or adjusted under 35 U.S.C. 154(b) by 1334 days.

(21) Appl. No.: 11/730,056

(22) Filed: Mar. 29, 2007

(65) Prior Publication Data

US 2007/0232890 A1  Oct. 4, 2007

(30) Foreign Application Priority Data

Mar. 30, 2006  (JP) ................................. 2006-096037

(51) Int. Cl.
*A61B 8/13*  (2006.01)

(52) U.S. Cl. ........ 600/462; 600/467; 600/445; 600/459; 600/466

(58) Field of Classification Search .................. 600/407, 600/424, 437, 443–447, 459, 462, 463, 466–467, 600/476–480; 128/899
See application file for complete search history.

(56) References Cited

U.S. PATENT DOCUMENTS

| 5,321,501 | A | 6/1994 | Swanson et al. |
| 5,325,859 | A | 7/1994 | Ishihara et al. |
| 6,315,722 | B1 | 11/2001 | Yaegashi |
| 6,350,238 | B1 * | 2/2002 | Olstad et al. ................... 600/437 |
| 6,947,787 | B2 * | 9/2005 | Webler .......................... 600/434 |

FOREIGN PATENT DOCUMENTS

| JP | 5-184576 A | 7/1993 |
| JP | 8-38470 A | 2/1996 |
| JP | 2000-279413 A | 10/2000 |
| JP | 2002-153472 A | 5/2002 |

* cited by examiner

*Primary Examiner* — Brian Casler
*Assistant Examiner* — Rajeev Siripurapu
(74) *Attorney, Agent, or Firm* — Buchanan Ingersoll & Rooney PC

(57) ABSTRACT

An image diagnostic system controls a probe to perform radial scanning within a body cavity and to acquire reflected signals through the probe. The system produces data based on the signals, constructs and outputs tomographic images of the body cavity and biotissue surrounding the body cavity. The system includes an extraction unit for extracting portions of the produced data on the basis of a frame rate upon successively outputting the tomographic images, and a first output control unit for forming, based on the extracted data, real time tomographic images of the body cavity and biotissue which are outputted in real time during radial scanning. A storage device stores the produced data, and a second output control unit forms, subsequent to the radial scanning, tomographic images of the body cavity and biotissue based on the stored data which are then outputted.

18 Claims, 26 Drawing Sheets

FIG. 7
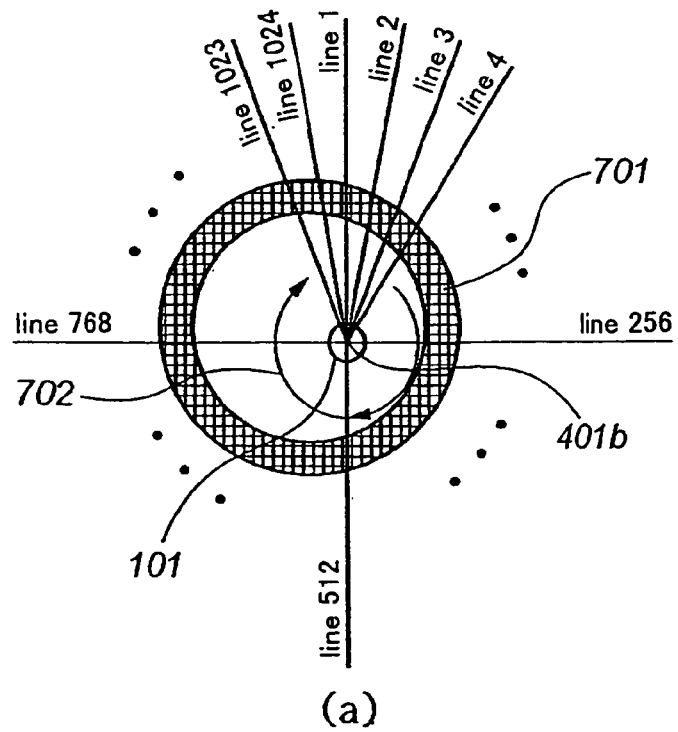
(a)
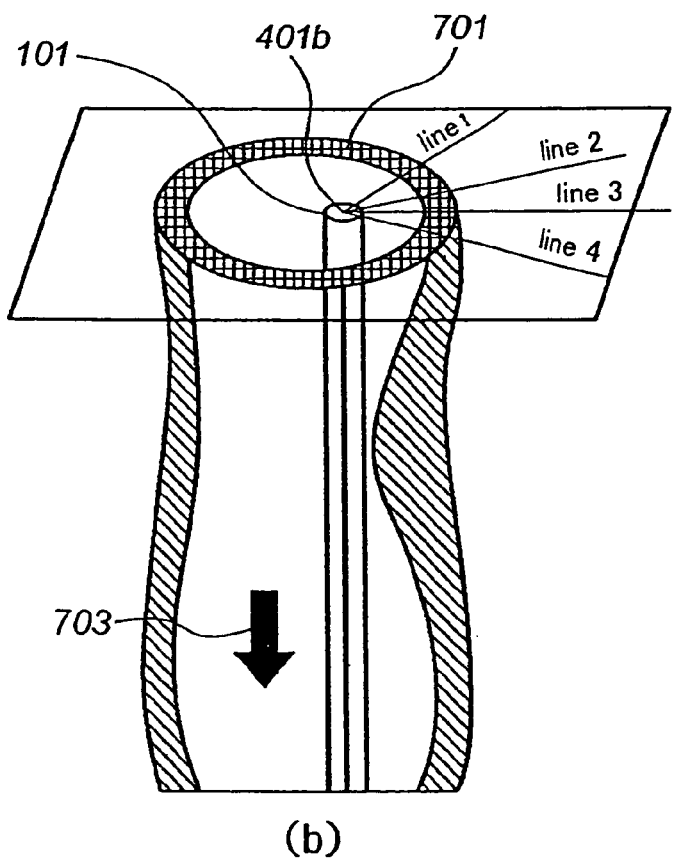
(b)

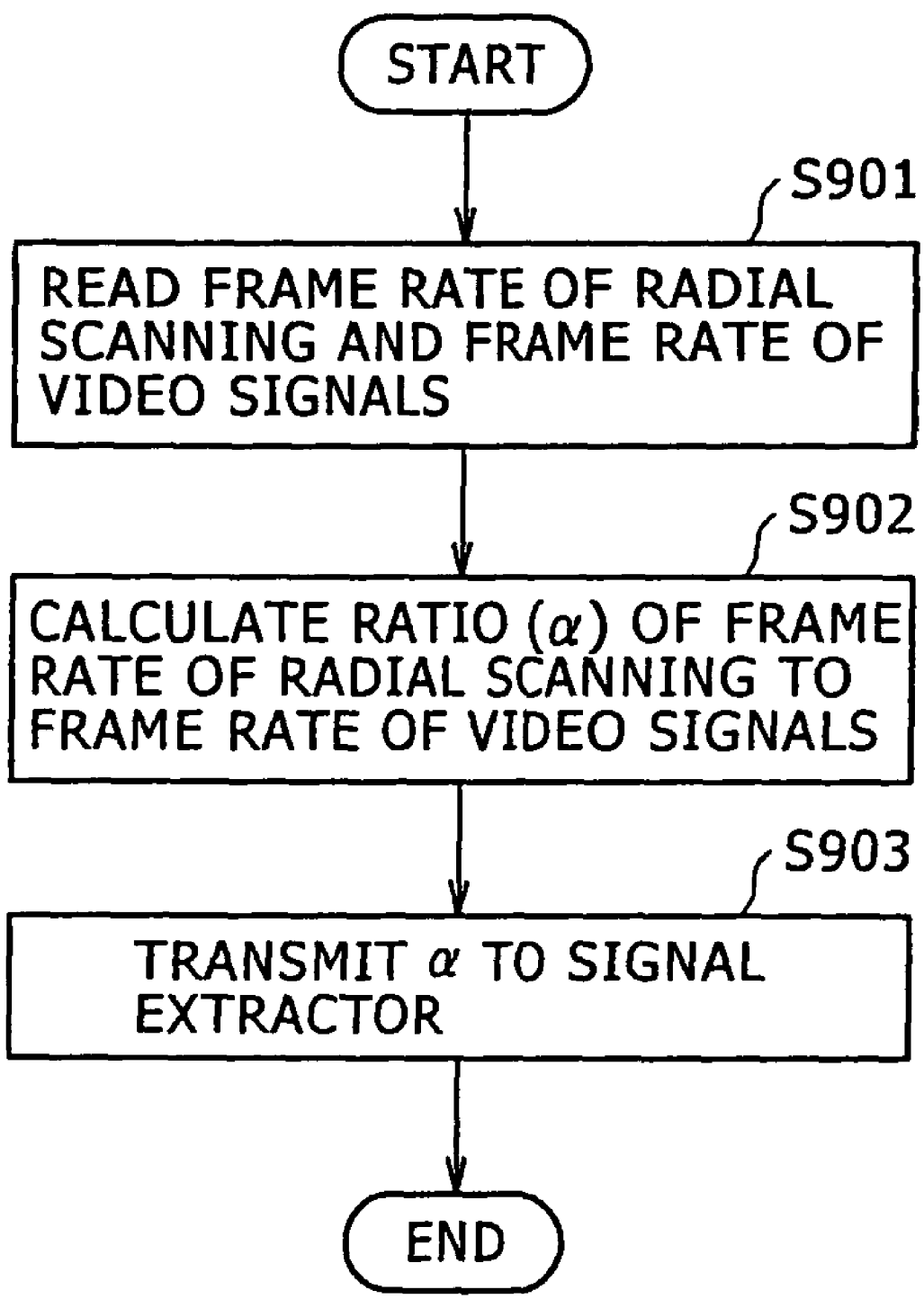

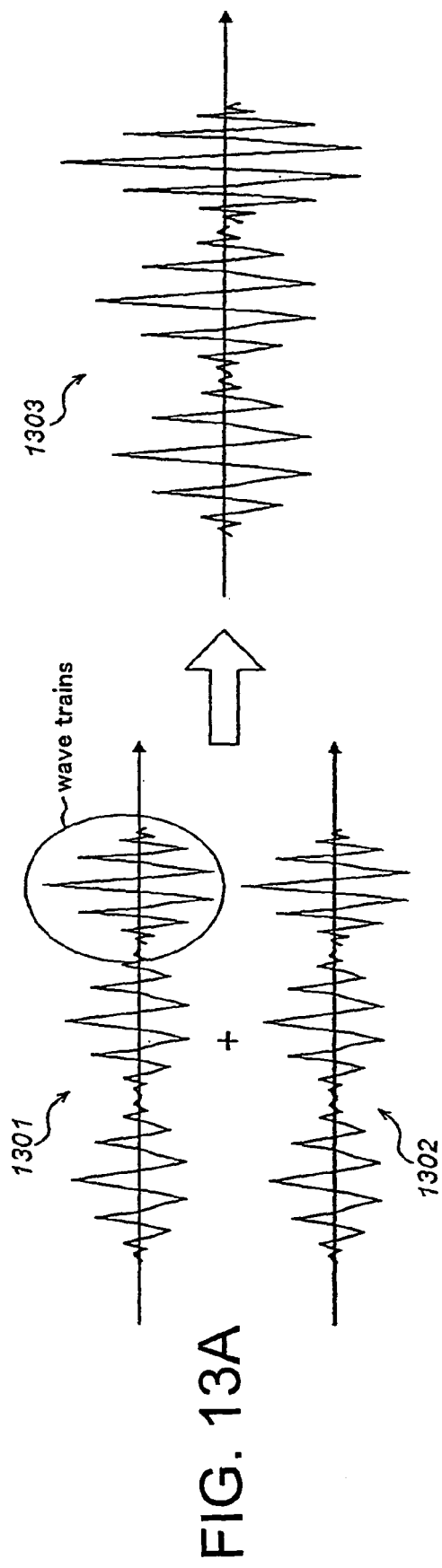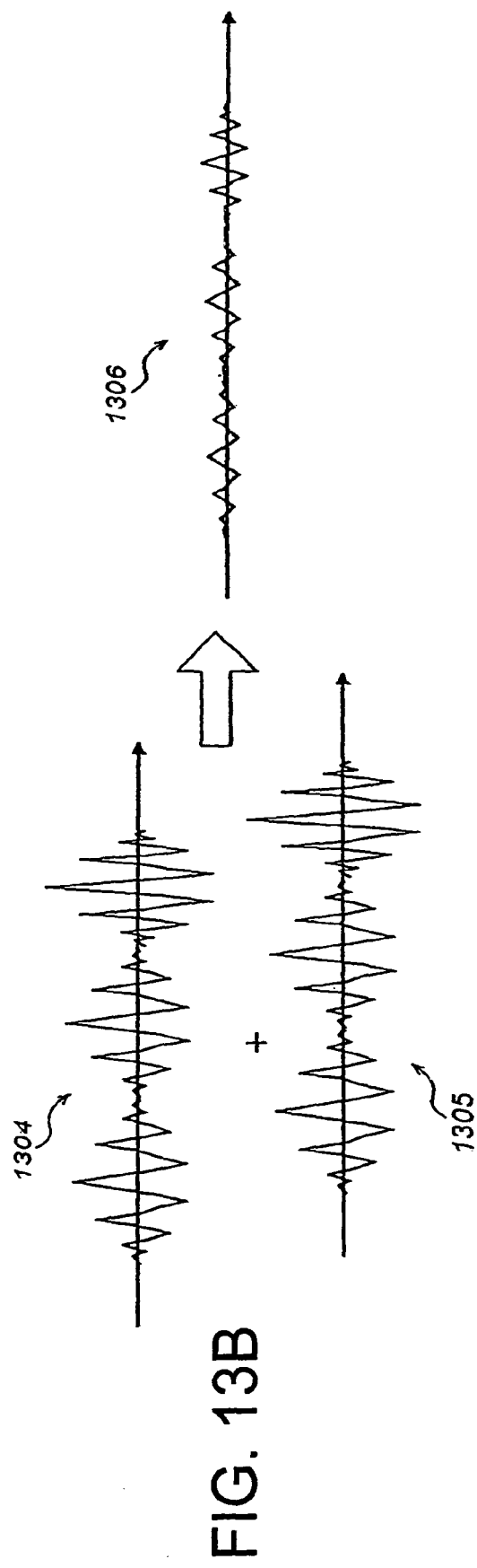

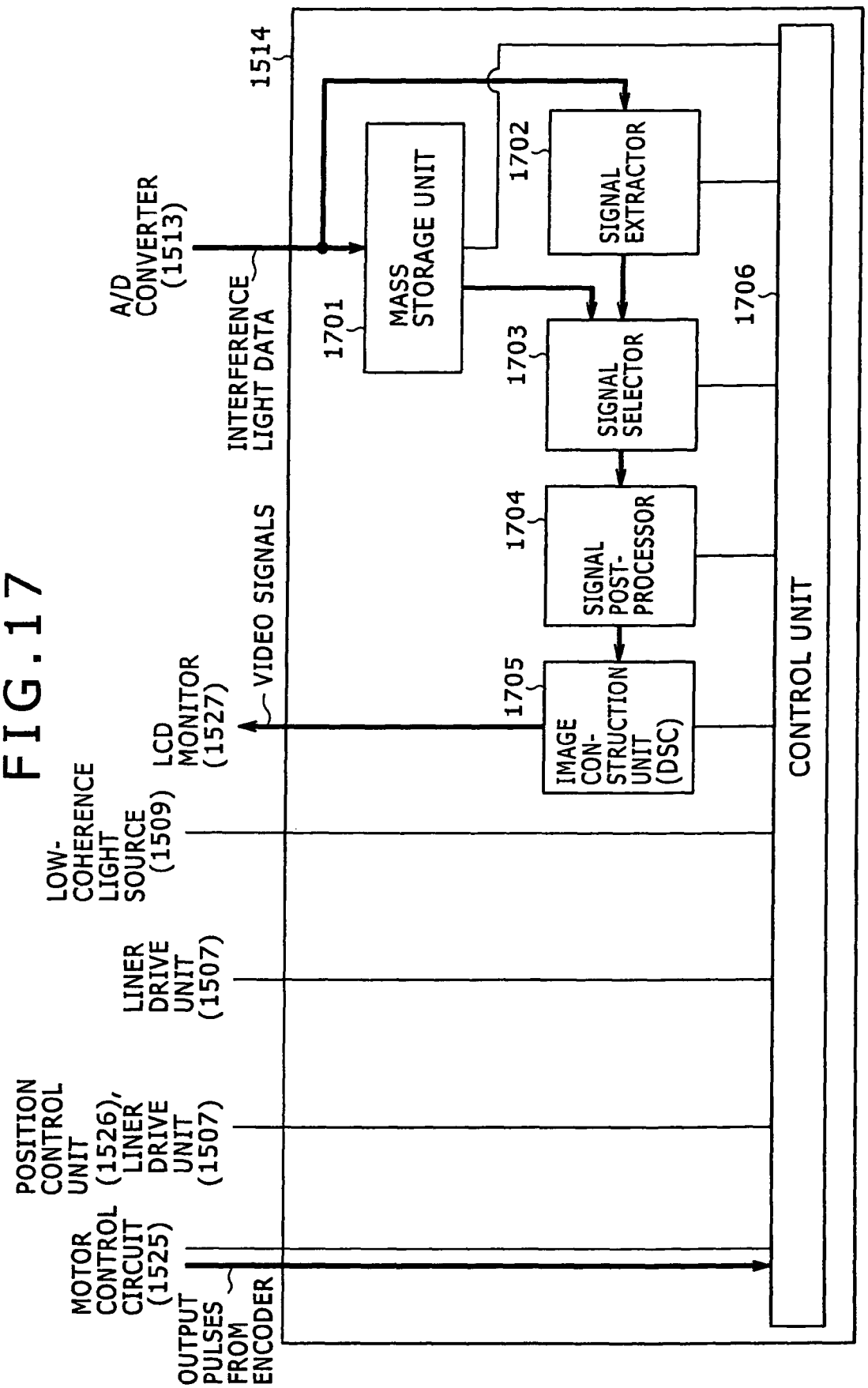

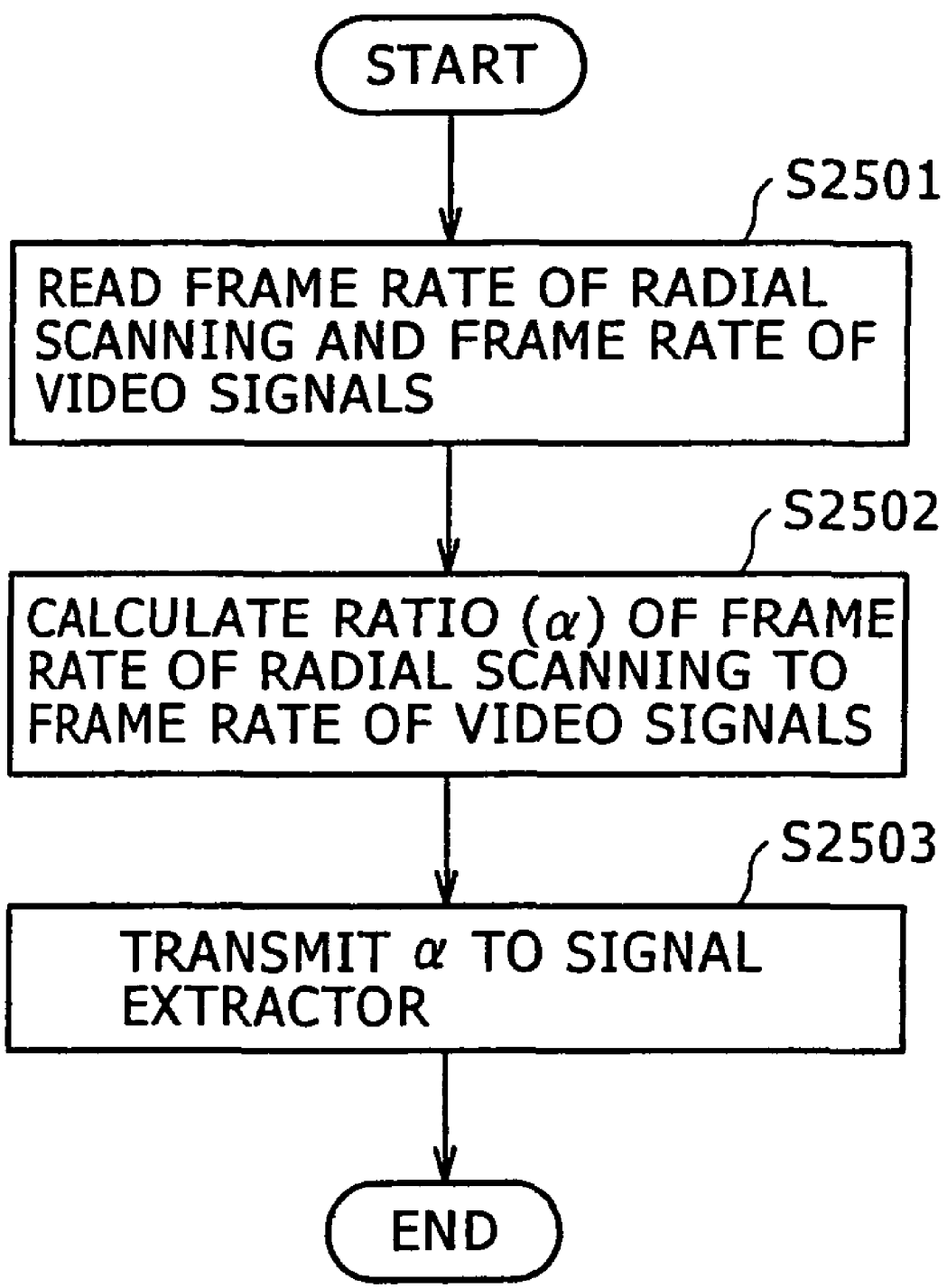

DIAGNOSTIC IMAGING SYSTEM AND PROCESSING METHOD FOR PRODUCING REDUCED FRAME RATE IMAGES FROM DATA COLLECTED AT A HIGHER FRAME RATES

TECHNICAL FIELD

This invention generally relates to an image diagnostic system and a processing method for such a system.

BACKGROUND DISCUSSION

Image diagnostic systems have been used for diagnosing arteriosclerosis, for preoperative diagnosis upon coronary intervention by a high-performance catheter such as a dilatation catheter (i.e., balloon catheter) or stent, and for assessing postoperative results.

Examples of these image diagnostic systems include intravascular ultrasound (IVUS) imaging systems. In general, the intravascular ultrasound imaging system is constructed to control an ultrasonic transducer to perform radial scanning within a blood vessel, to receive a reflected wave(s) (ultrasound echoes) reflected by biotissue (e.g. the blood vessel wall) by the same ultrasonic transducer, to subject the reflected waves to processing such as amplification and detection, and then to construct and display a tomographic image of the blood vessel on the basis of the intensities of the received ultrasound echoes.

In addition to these intravascular ultrasound imaging systems, optical coherence tomography (OCT) imaging systems have been developed in recent years for use as image diagnostic systems. In an OCT imaging system, a catheter with an optical fiber incorporated therein is inserted into a blood vessel. The distal end of the optical fiber is provided with an optical lens and an optical mirror. Light is emitted in the blood vessel while radially scanning the optical mirror arranged on the side of the distal end of the optical fiber, and based on light reflected from biotissue forming the blood vessel, a tomographic image of the blood vessel is then constructed and displayed.

Improved OCT imaging systems have been proposed in recent years which make use of a wavelength swept light source.

As described above, image diagnostic systems include several different kinds of systems which use different detection principles. Nonetheless, they are all characterized in that a tomographic image (i.e. cross-sectional image) is constructed and displayed by performing radial scanning with a probe. Accordingly, these image diagnostic systems each have merit in that the time required for a diagnosis by the system can be shortened by making radial scanning faster to increase the scanning speed in the axial direction.

A specific description will be made about an IVUS imaging system as an example. With the IVUS imaging system, tomographic images are generally extracted by performing radial scanning to transmit and receive ultrasounds while rotating an ultrasonic transducer at 1,800 rpm or so.

The setting at 1,800 rpm or so is attributed to the fact that the frame rate of video signals for successively outputting images to a display such as a CRT or LCD is 30 fps (30 frames/sec=1,800 frames/min) in many instances. Therefore, no additional tomographic image or images can be outputted to the side of the display even if the radial scanning is performed at a higher speed.

However, 1/30 second is needed to scan one frame of a tomographic image when the rotational speed of the ultrasonic transducer is 1,800 rpm or so. In this case, an image blur may occur by a heart beat while scanning one frame of the tomographic image. Faster radial scanning is hence desired.

As mentioned above, however, such faster radial scanning is still incapable of displaying acquired images in real time unless the frame rate of video signals for the display is made faster. Therefore, it may be possible to contemplate, for example, such a display method that without real-time construction of tomographic images, received signals are all converted into digital data by an A/D converter and once stored in a mass storage device such as a hard disk or semiconductor memory, and subsequent to completion of the data acquisition, all frames of the tomographic images are constructed from the recorded data and are then displayed.

For example, U.S. Pat. No. 6,315,722 discloses a method in which data produced based on received signals of ultrasounds are all stored in real time in a mass storage device such as a hard disk.

It is, however, impossible to confirm in real time whether or not data have been normally acquired, if the method disclosed in U.S. Pat. No. 6,315,722 is used to once store all the data without real-time construction and display of tomographic images and subsequent to the completion of the acquisition of the data, to construct and display all frames of tomographic images.

If data cannot be acquired for one reason or another, it thus becomes necessary to reinsert a catheter into the patient and to acquire data. This is certainly inconvenient. Further, the incapability of real-time confirmation of tomographic images as a result of the adoption of faster radial scanning by the probe is not well suited as an image diagnostic system.

SUMMARY

According to one aspect, an image diagnostic system comprises a probe positionable in a body cavity and configured to repeatedly transmit signals into a body cavity and receive reflected signals which are reflected by biotissue surrounding the body cavity during radial scanning, a main control unit configured to produce data based on the reflected signals to construct tomographic images of the body cavity and biotissue, and a display unit configured to display the tomographic images of the body cavity and biotissue. The main control unit comprises an extraction unit configured to extract portions of the produced data based on a frame rate of the display unit, a first output control unit configured to form, based on the extracted portions of the data extracted by the extraction unit, real time tomographic images of the body cavity and biotissue and to output the real time tomographic images during the radial scanning, a storage device configured to store the produced data, and a second output control unit configured to form and output, based on the data stored in the storage device, successive tomographic images after the radial scanning.

According to another aspect, an image diagnostic system comprises a probe positionable in a body cavity and configured to repeatedly transmit signals into a body cavity and receive reflected signals which are reflected by biotissue surrounding the body cavity during radial scanning, a main control unit configured to produce data based on the reflected signals to construct tomographic images of the body cavity and biotissue, a display unit configured to display the tomographic images of the body cavity and biotissue, the display, and a motor connected to the probe to rotate the probe during the radial scanning at a frame rate faster than a display frame rate of the display unit. The main control unit comprises a storage device configured to store the produced data associated with each rotation of the probe, an extraction unit configured to extract either only a portion of the produced data associated with each rotation of the probe or the produced data associated with only some rotations of the probe, and a first output control unit configured to form real time tomographic images of the body cavity and biotissue based on the data extracted by the extraction unit, and to output the real time tomographic images during the radial scanning.

Another aspect involves an image diagnostic apparatus for controlling a probe, which is adapted to be connected to the image diagnostic apparatus and which repeatedly transmits signals into a body cavity which are reflected by biotissue surrounding the body cavity to perform radial scanning within the body cavity. The image diagnostic apparatus comprises a main control unit configured to produce data based on the reflected signals and to construct a tomographic image of the body cavity and the biotissue surrounding the body cavity on a basis of the produced data, and a display unit configured to display the tomographic images. The main control unit comprises an extraction unit configured to extract portions of the produced data based on a frame rate of the display unit, a first output control unit configured to form, based on the extracted data, real time tomographic images of the body cavity and biotissue, and to output the real time tomographic images during the radial scanning, a storage device configured to store the produced data, and a second output control unit configured to form, based on the data stored in the storage device, successive tomographic images and to output the tomographic images after the radial scanning.

Also disclosed is a method for processing information in an image diagnostic system connected to a probe to produce tomographic images to be displayed on a display unit. The method comprises transmitting signals from the probe into a body cavity and receiving signals reflected from biotissue surrounding the body cavity during radial scanning, producing data based on the received reflected signals, extracting portions of the produced data based on a frame rate of the display unit, forming real time tomographic images of the body cavity and the biotissue based on the extracted data, and outputting the real time tomographic images during the radial scanning, storing the produced data, and forming tomographic images of the body cavity and the biotissue based on the produced data that has been stored and outputting the tomographic images subsequent to the radial scanning.

According to another aspect, a method for producing tomographic images of a body cavity and surrounding biotissue comprises positioning a probe in a body cavity, transmitting signals from the probe into the body cavity and receiving signals reflected from the biotissue surrounding the body cavity while rotating the probe at a frame rate to perform radial scanning, producing data based on the received reflected signals, extracting either only a portion of the produced data associated with each rotation of the probe or the produced data associated with only some rotations of the probe, forming real time tomographic images of the body cavity and biotissue based on the extracted data, and displaying the real time tomographic images during the radial scanning at a frame rate less than the frame rate of the probe during the radial scanning.

With the system, apparatus and method disclosed here, the real-time output of images can be performed even when radial scanning by the probe is increased or made faster.

Also disclosed is a recording medium with a control program stored therein for performing by a computer the disclosed method and a control program for performing by a computer the method.

BRIEF DESCRIPTION OF THE DRAWING FIGURES

The foregoing and additional aspects of the disclosed system and method will become more apparent from the following detailed description considered with reference to the accompanying drawing figures briefly described below.

FIGS. 7A and 7B are perspective views in cross-section of a blood vessel and the catheter section inserted therein, illustrating movements of the catheter section during an intravascular ultrasound diagnosis.

FIG. 9 is a flow chart showing operational aspects of a control unit upon conducting a real-time display in an intravascular ultrasound diagnosis.

FIGS. 13A and 13B are waveform diagrams illustrating the principle of a measurement by an OCT imaging system according to a third embodiment of the present invention.

FIG. 17 is a block diagram schematically depicting operational aspects of a signal processor in the OCT imaging system.

FIG. 25 is a flow chart showing operational aspects of processing at a control unit upon conducting a real-time display in optical coherence tomography making use of a wavelength swept light source.

DETAILED DESCRIPTION

First Embodiment

1. General Overall Construction of IVUS Imaging System

Figure 1:
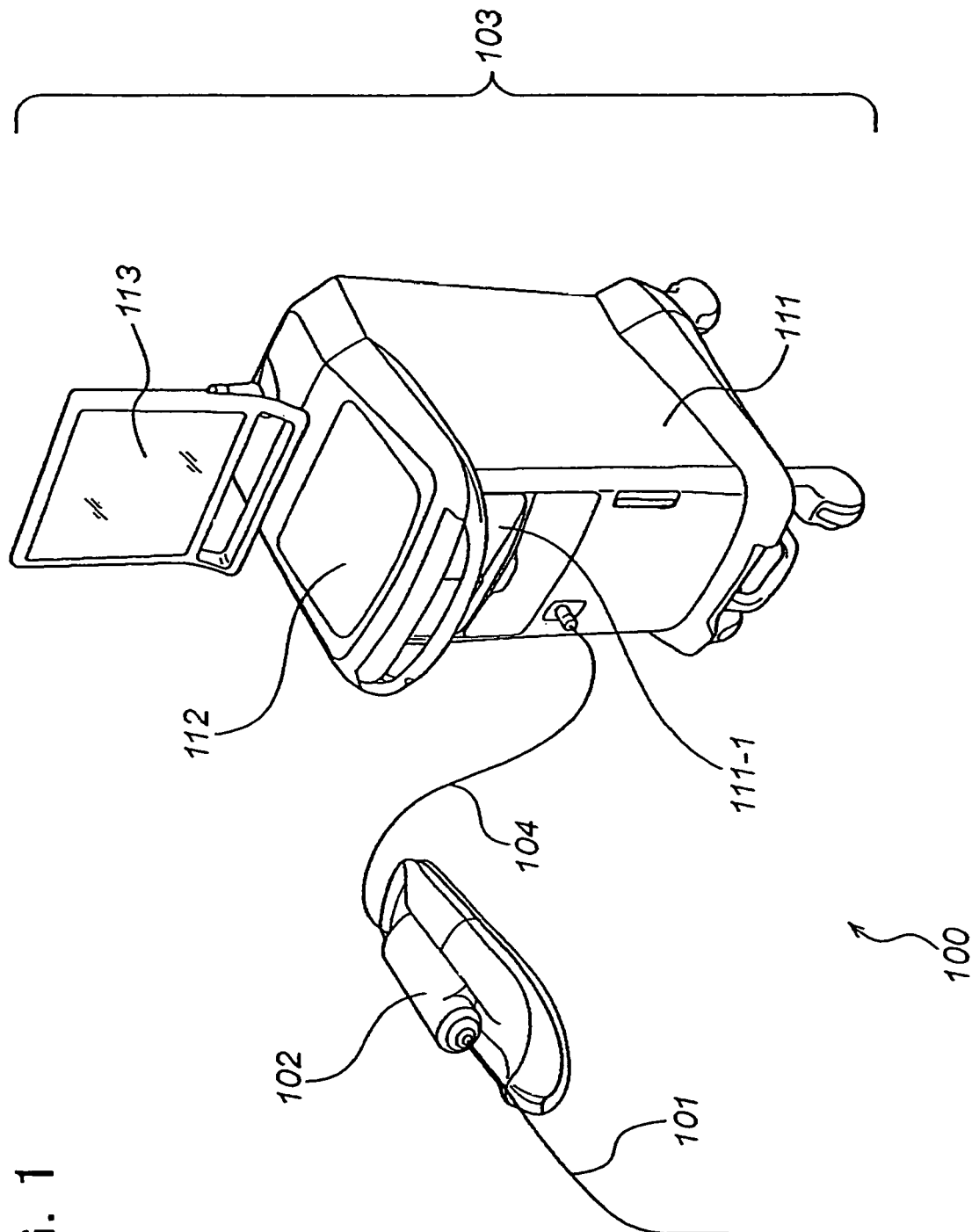
FIG. 1 is a perspective view generally illustrating aspects and features of an IVUS imaging system according to a first embodiment disclosed herein.

Referring to FIG. 1, an intravascular ultrasound (IVUS) imaging system (i.e., image diagnostic system) 100 according to one illustrated and disclosed embodiment includes a catheter section (i.e., probe) 101, a scanner & pull-back unit 102 and an operation control system 103. The scanner & pull-back unit 102 and the operation control system 103 are connected together via a signal line 104 and compose an image diagnostic apparatus.

Figure 4:
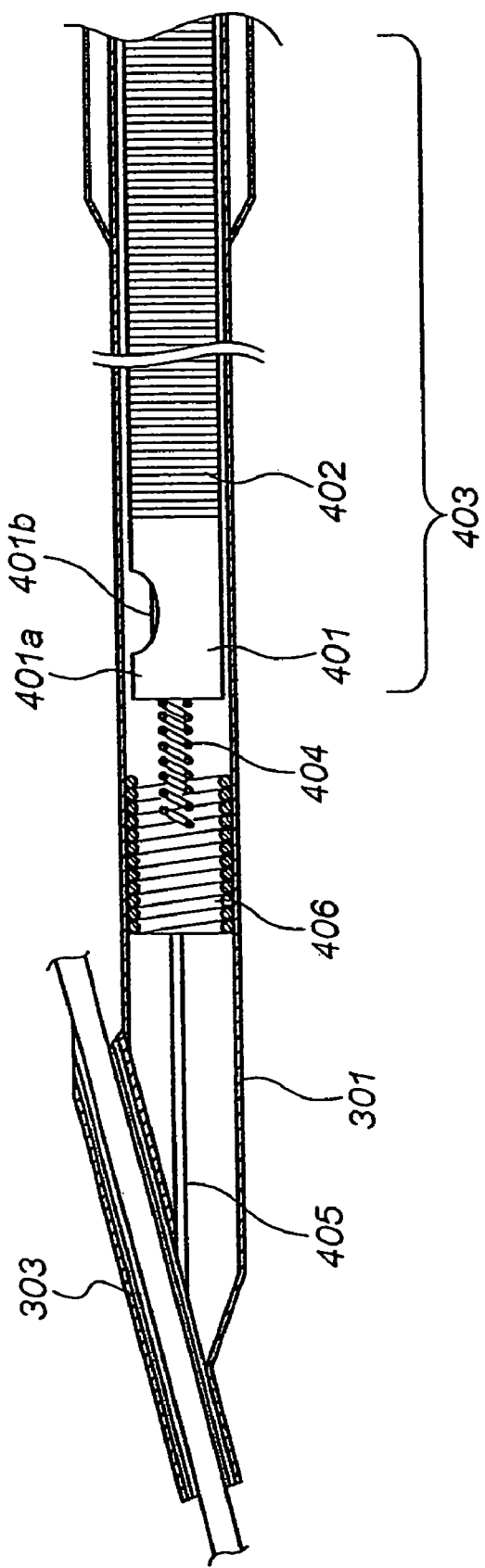
FIG. 4 is a cross-sectional view of the distal end portion of the catheter section shown in FIG. 3.

The catheter section 101 is adapted to be inserted directly into a blood vessel to measure internal conditions of the blood vessel by way of an ultrasonic transducer 401b which is shown in FIG. 4. The scanner & pull-back unit 102 controls movements of the ultrasonic transducer 401b within the catheter section 101.

The operation control system 103 includes a main control unit 111 which performs processing of data acquired by a measurement and outputs the results of the processing, and a printer & DVD recorder 111-1 which prints the results of the processing in the main control unit 111 or records (i.e., stores) them as data.

The operation control system 103 also includes a control panel 112. Through the control panel 112, a user is able to input various values such as preset values. In addition, the operation control system 103 includes an LCD monitor 113 (i.e., display) which displays the results of the processing in the main control unit 111.

2. Aspects and Features of IVUS Imaging System

Figure 2:
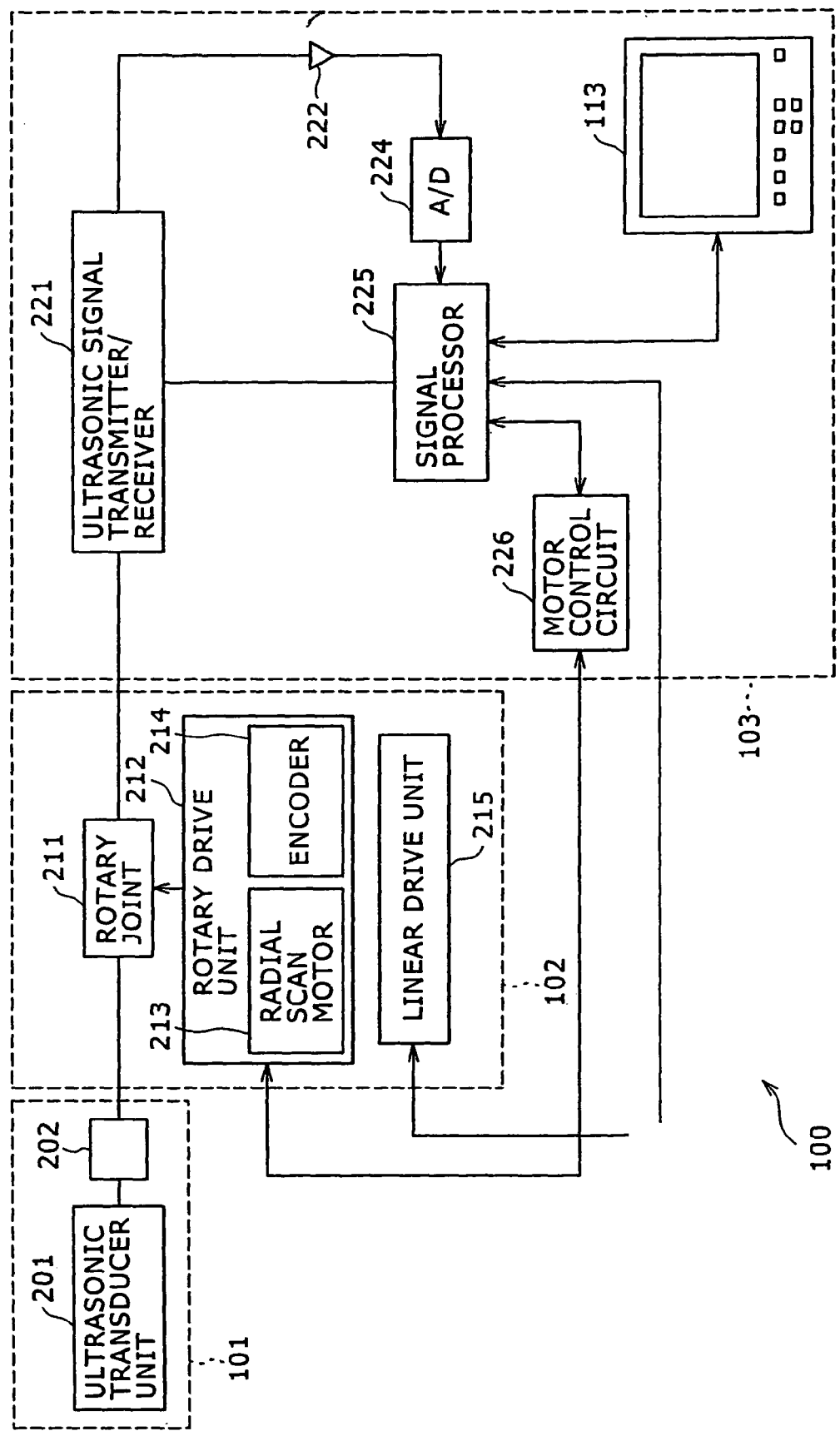
FIG. 2 is a block diagram schematically illustrating additional aspects and features of the IVUS imaging system.

FIG. 2 schematically illustrates in more detail aspects and features of the IVUS imaging system 100 illustrated in FIG. 1. The distal end of the catheter section 101 is internally provided with an ultrasonic transducer unit 201. With the distal end of the catheter section 101 inserted within a blood vessel, the ultrasonic transducer 201, responsive to a pulse wave transmitted by an ultrasonic signal transmitter/receiver 221, transmits ultrasound in the direction of a section of the blood vessel, and receives the reflected signals (echoes) and transmits them as ultrasonic echo signals to the ultrasonic signal transmitter/receiver 221 via a connector 202 and a rotary joint 211.

The scanner & pull-back unit 102 includes the rotary joint 211, a rotary drive unit 212 and a linear drive unit 215. The ultrasonic transducer unit 201 within the catheter section 101 is rotatably mounted by the rotary joint 211, which connects a non-rotatable block and a rotatable block with each other, and is rotationally driven by a radial scan motor 213. Rotation of the ultrasonic transducer unit 201 in a circumferential direction within the blood vessel makes it possible to detect ultrasound echo signals required for the construction of a tomographic image of the blood vessel at the predetermined position within the blood vessel.

The operation of the radial scan motor 213 is controlled based on a control signal transmitted from a signal processor 225 via a motor control circuit 226. Further, each rotation angle of the radial scan motor 213 is detected by an encoder 214. Each output pulse outputted at the encoder 214 is inputted in the signal processor 225, and is used as a timing for the reading of signals to be displayed.

The scanner & pull-back unit 102 includes the linear drive unit 215 and, based on an instruction from the signal processor 225, specifies movements of the catheter section 101 in the direction of its insertion.

The ultrasonic signal transmitter/receiver 221 includes a transmission circuit and a reception circuit (not shown). Based on a control signal transmitted from the signal processor 225, the transmission circuit transmits a pulse wave to the ultrasonic transducer unit 201 in the catheter section 101.

The reception circuit, on the other hand, receives ultrasonic signals from the ultrasonic transducer unit 201 in the catheter section 101. The thus-received ultrasonic signals are amplified by an amplifier 222.

At an A/D converter 224, the ultrasonic signals outputted from the amplifier 222 are sampled to produce digital data (ultrasound echo data) for one line.

Ultrasound echo data produced in line units at the A/D converter 224 are inputted into the signal processor 225. The signal processor 225 detects the ultrasound echo data, constructs tomographic images of the blood vessel at respective positions within the blood vessel, and outputs them at a predetermined frame rate to the LCD monitor 113.

Figure 3:
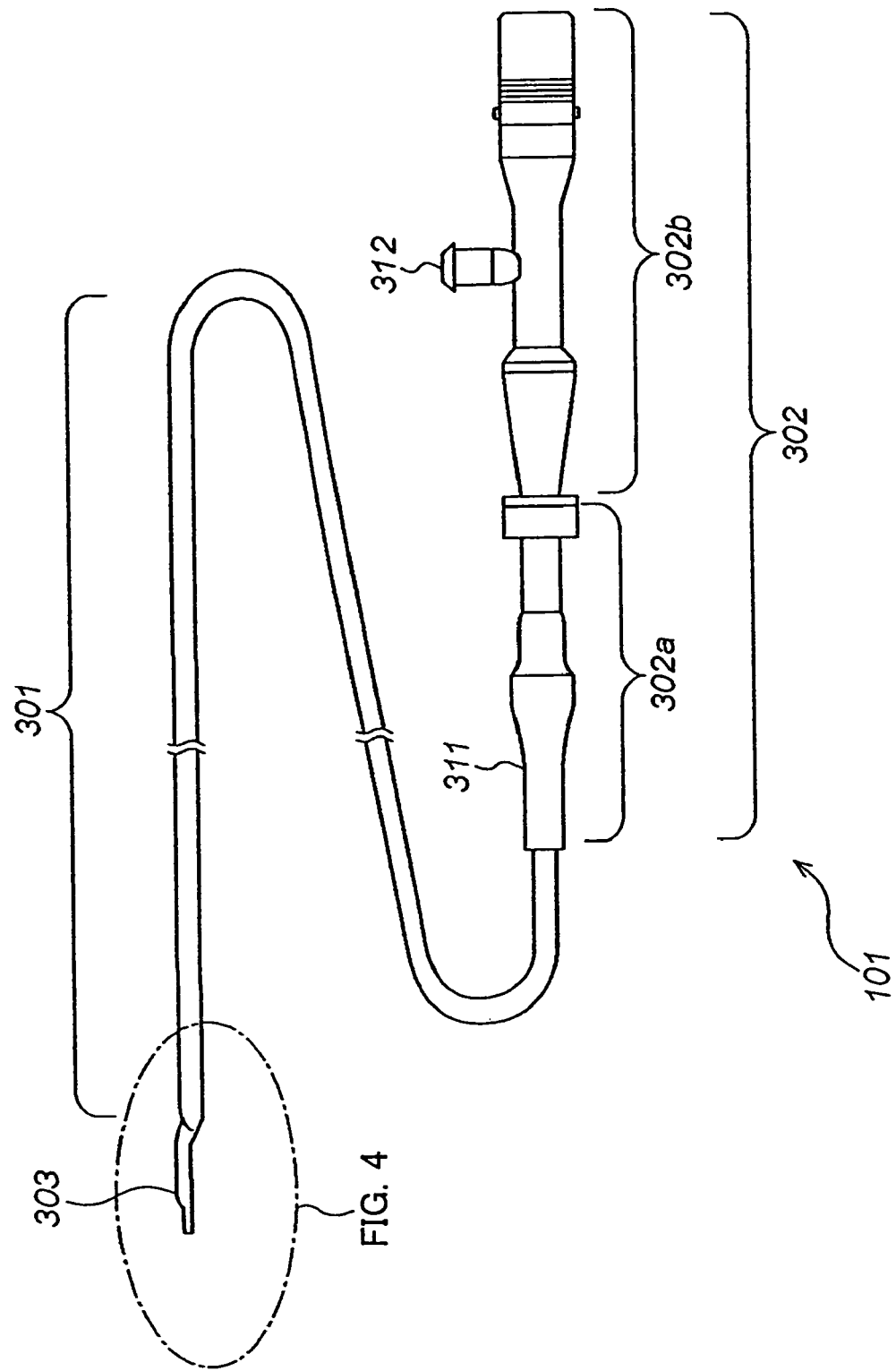
FIG. 3 is a perspective view of the overall construction of a catheter section in the IVUS imaging system.

3. Construction of Catheter Section 3.1 Overall Construction of Catheter Section The overall general construction of the catheter section 101 is illustrated in FIG. 3. The catheter section 101 is constructed as an elongated catheter sheath 301 adapted to be inserted into a blood vessel and a connector 302, not inserted into the blood vessel, that is arranged on the side of the user's hand to permit handling and operation by the user. A guidewire lumen 303 is provided at the distal end of the sheath 301. Within the catheter sheath 301 is a lumen which continuously extends from a connecting portion with the guidewire lumen 303 to a connecting portion with the connector 302.

The connector 302 is composed of a sheath connector 302a and a driveshaft connector 302b. The sheath connector 302a is constructed integrally with the proximal end of the catheter sheath 301. The driveshaft connector 302b is arranged on the proximal end of a driveshaft, which will be described below, to rotatably hold the drive shaft.

An anti-kink protector 311 is arranged at a boundary portion between the sheath connector 302a and the catheter sheath 301. The arrangement of this anti-kink protector 311 makes it possible to maintain a predetermined degree of stiffness, thereby helping to prevent short tight twist or curl which might otherwise be caused by a sudden change in torque. The driveshaft connector 302b is provided with an injection port 312 to which a syringe (not illustrated) or the like can be attached to fill up the lumen of the catheter sheath 301 in its entirety with an ultrasound transmission liquid (e.g., saline). The proximal end of the driveshaft connector 302b is constructed to be connected to the scanner & pull-back unit 102.

3.2 Construction of Distal End Portion of Catheter Section

FIG. 4 illustrates in more detail the distal end portion of the catheter section 101. Through the lumen of the catheter sheath 301, an imaging core 403 extends over substantially the entire length of the catheter sheath 301. The imaging core 403 is provided with an ultrasonic transducer unit 401 for transmitting and receiving ultrasound and also includes the driveshaft 402 for transmitting drive force to rotate the ultrasonic transducer unit 401. The ultrasonic transducer unit 401 is comprised of an ultrasonic transducer 401b and a housing 401a in which the ultrasonic transducer 401b is held. Ultrasound is transmitted from the ultrasonic transducer 401b toward the surrounding biotissue of a body cavity, and reflected waves from the surrounding biotissue of the body cavity are received at the ultrasonic transducer 401b.

The driveshaft 402 is constructed in the form of a coil, accommodates a signal line therein, and extends from the ultrasonic transducer 401b to the connector 302.

The ultrasonic transducer 401b possesses a rectangular or circular shape, and is formed by depositing electrodes on opposite sides of a piezoelectric member made of PZT or the like. The ultrasonic transducer 401b is arranged to assume a position around the central axis of rotation to prevent the driveshaft 402 from causing rotational fluctuations.

The housing 401a is in the form of a short cylindrical tube provided at a part thereof with a cut-off portion. Examples of materials forming the housing 401a include metal or hard resin. Examples of methods for forming the housing 401a include machining such as cutting, laser machining or pressing a tubular material to form the cut-off portion, or the desired shape may be directly obtained by injection molding, MIM (metal injection molding) or the like. The ultrasonic transducer 401b is carried in the housing 401a. The proximal end side of the housing 401a is connected with the driveshaft 402. A resilient member 404 in the form of a short coil is arranged on the distal end side of housing 401a.

The resilient member 404 is coil-shaped wire which can be produced by forming a stainless steel wire into a coiled shape. The arrangement of the resilient member 404 on the distal end side of the housing 401a provides the imaging core 403 with improved stability upon rotation. Gold plating can be applied to a surface of the resilient member 404 or the housing 401a. As gold is a metal having high x-ray opacity, the gold plating permits visualization of the resilient member 404 in an image taken by an x-ray imaging system (i.e., radiopaque) when the catheter sheath 301 is inserted into a body cavity. As a consequence, the user can easily ascertain the position of the ultrasonic transducer 401b.

At a boundary portion between the distal end portion of the catheter sheath 301 and the guidewire lumen 303, a discharge channel 405 is arranged to discharge the ultrasound transmission fluid injected during priming.

A reinforcement coil 406 is arranged inside the catheter sheath 301 to assist in preventing kinking of the distal end portion of the catheter sheath 301.

The guidewire lumen 303 has a bore adapted to receive a guidewire. The guidewire is inserted beforehand in a body cavity and is utilized to guide the catheter sheath 301 to a diseased part.

The driveshaft 402 is constructed of a multiple or multilayer, tight coil or the like having properties such that it can rotate and axially move (i.e., slide) relative to the catheter sheath 301, is flexible, and can relatively smoothly transmit rotation. The multiple or multilayer, tight coil or the like may be made, for example, of a wire of a metal such as stainless steel.

Owing to the rotation of the driveshaft 402, the lumen can be observed over 360 degrees. To perform an observation over a still greater range, it is only necessary to slide (pull back) the driveshaft 402 in the axial direction.

Figure 5:
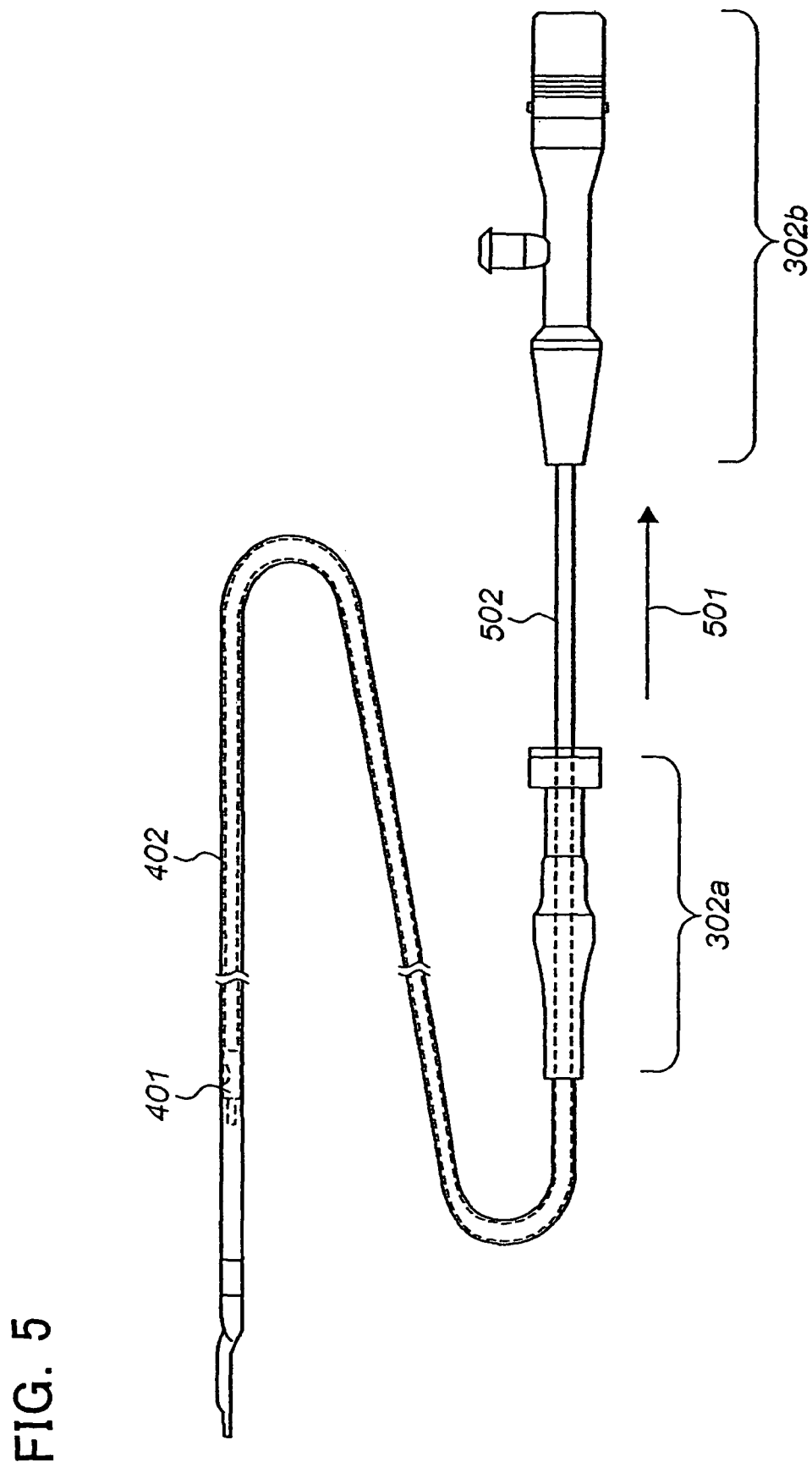
FIG. 5 is a perspective view of the catheter section showing the manner of sliding a driveshaft relative to a catheter sheath in the catheter section.

FIG. 5 schematically illustrates the manner in which the driveshaft 402 is slidably advanced relative to the catheter sheath 301. The sliding of the driveshaft connector 302b toward its proximal end (in the direction of arrow 501) with the sheath connector 302a held fixed causes the driveshaft 402, which is accommodated within and fixed to the driveshaft connector 302b, and the ultrasonic transducer unit 401, which is fixedly secured on the distal end of the driveshaft 402, to also slide in the axial direction. This axial sliding may be effected either manually by the user or by an electrical drive. On the distal end side of the driveshaft connector 302b, a protecting inner tube 502 is arranged to avoid exposure of the driveshaft 402 which rotates at a high speed.

4. Features of the Signal Processor

Figure 6:
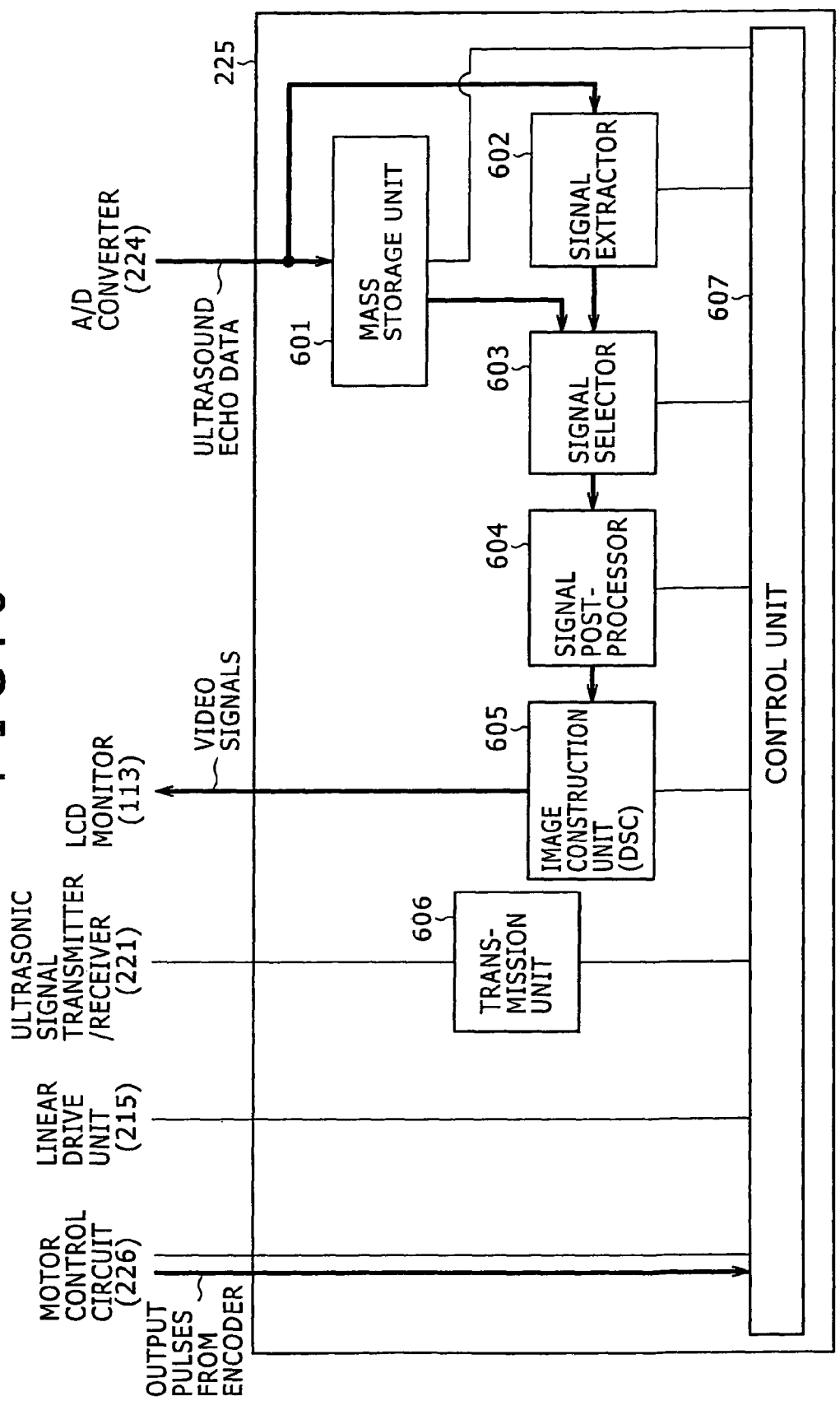
FIG. 6 is a block diagram schematically illustrating aspects of a signal processing unit in the IVUS imaging system.

Various aspects of the signal processor 225 forming a part of the operation control system 103 of the IVUS imaging system 100 are illustrated in FIG. 6. The signal processor 225 includes a control unit 607 which systematically controls the IVUS imaging system 100 in its entirety, and a transmission unit 606 which transmits operating instructions to the ultrasonic signal transmitter/receiver 221.

The signal processor 225 also includes a mass storage unit (i.e., storage device) 601 which is composed of a hard disk, semiconductor memory or the like. At the mass storage unit 601, ultrasound echo data transmitted from the ultrasonic signal transmitter/receiver 221 via the amplifier 222 and A/D converter 224 are successively received on a transmission/reception unit (line unit) basis, and are stored.

The ultrasound echo data stored in the mass storage unit 601 are read in accordance with a frame rate of video signals as needed (based on instructions from the control unit 607), and are then fed to a signal selector 603.

The capacity of the mass storage unit 601 is determined depending on how many frames of data are to be acquired by radial scanning. When a 150 mm blood vessel is subjected to radial scanning at a pitch of 0.5 mm, for example, 300 frames of data are acquired. If each frame consists of 16-bit data of 1,024 lines×1,024 samples, the total data size becomes 600 Mbytes. In this case, a semiconductor memory or hard disk of 1 Gbytes or greater can be chosen as the mass storage unit 601.

A signal extractor (i.e., extraction unit) 602 forming a part of the signal processor 225 operates to selectively extract predetermined data from the ultrasound echo data transmitted from the A/D converter 224. The signal extractor 602 can be composed of an FIFO (first in, first out) memory with a write inhibit function. In synchronization with each output pulse from the encoder 214, the write enable/disable status of the FIFO memory is controlled. Only when the FIFO memory is writable, inputted ultrasound echo data are written in the FIFO memory.

More specifically, the FIFO memory is made writable in transmission/reception unit (line unit) so that data corresponding to radial scanning for one frame can be constructed. If unnecessary ultrasound echo data are inputted, the FIFO memory is write-disabled. Reading from the FIFO memory is performed in synchronization with a timing of subsequent processing, and the thus-read ultrasound echo data are outputted to the signal selector 603. Additional details associated with an extraction method of ultrasound echo data are described below.

When the signal selector 603 receives from the control unit 607 an instruction to the effect that the ultrasound echo data stored in the mass storage unit 601 are to be read, the signal selector 603 reads the ultrasound echo data from the mass storage unit 601, and transmits them to a signal post-processor 604. When the signal selector 603 receives from the control unit 607 an instruction of a real-time image display, on the other hand, the signal selector 603 reads the ultrasound echo data extracted at the signal extractor 602, and transmits them to the signal post-processor 604.

The signal post-processor 604 performs processing such as logarithmic conversion, frame correlation, gamma correction, contrast adjustment and sharpness filtering on the ultrasound echo data transmitted from the signal selector 603, and outputs the resulting data to an image construction unit 605.

At the image construction unit 605, streams of ultrasound echo data in the transmission/reception units (line units) of ultrasound are converted into video signals. Based on the video signals, tomographic images to be displayed on the LCD monitor 113 are constructed.

As a result, when the signal selector 603 receives from the control unit 607 an instruction to the effect that the ultrasound echo data stored in the mass storage unit 601 are to be read, the tomographic images formed based on the ultrasound echo data stored in the mass storage unit 601 are displayed on the LCD monitor 113. When an instruction for a real-time display of images is received, on the other hand, tomographic images formed based on the ultrasound echo data extracted at the signal extractor 602 are displayed corresponding to the radial scanning by the ultrasonic transducer 401*b*. In other words, control is effected such that the LCD monitor 113 performs two types of tomographic image displays as moving image, one being a real-time display during radial scanning and the other a display after the radial scanning.

5. Operation of the Catheter Section 101 upon Intravascular Ultrasound Diagnosis FIGS. 7A and 7B schematically illustrate movements of the catheter section 101 during an intravascular ultrasound (IVUS) diagnosis. FIG. 7A shows a section of a blood vessel 701 in which the catheter section 101 has been inserted. As described above, the ultrasonic transducer 401*b* is internally mounted at the distal end of the catheter section 101, and is rotated in the direction of arrow 702 by the radial scan motor 213.

From the ultrasonic transducer 401*b*, the transmission/reception of ultrasound is performed at respective rotation angles. Lines 1, 2, . . . , 1024 indicate the transmitting directions of ultrasound at the respective rotation angles. In this embodiment, 1,024 transmissions/receptions are intermittently performed while the ultrasonic transducer 401*b* rotates over 360 degrees in a predetermined blood vessel section (701). The number of transmissions/receptions of ultrasound during 360-degree rotation is not limited specifically to 1,024 but can be set as desired. The scanning that is repeated with the transmission/reception of a signal while rotating the ultrasonic transducer 401*b* as described above is generally called "radial scan" or "radial scanning".

Such transmissions/receptions of ultrasound are performed while advancing in the direction of arrow 703 (in FIG. 7B) through the blood vessel.

6. Signal Processing During an Intravascular Ultrasound Diagnosis 6.1 Outline of Signal Processing FIGS. 8A and 8B schematically outline operational aspects of the signal processing in the IVUS imaging system 100 during an intravascular ultrasound diagnosis according to this embodiment.

Figure 8A:
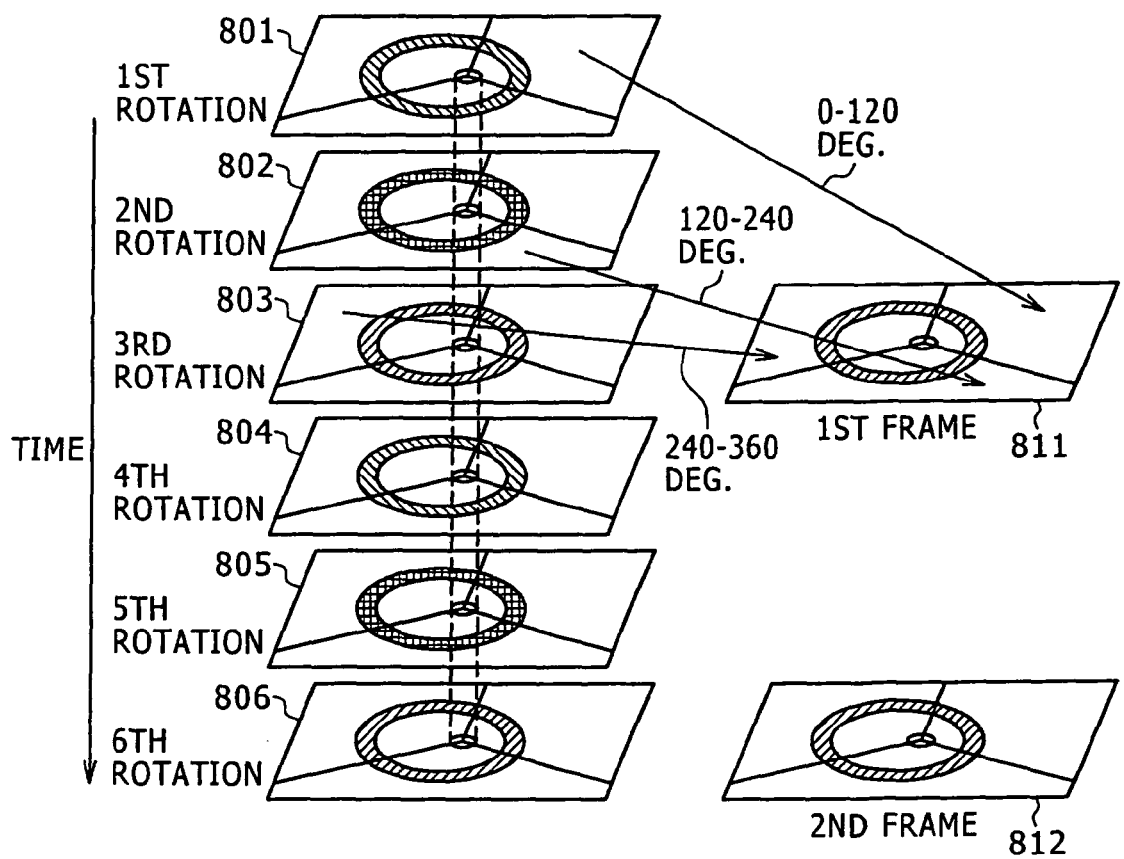
FIGS. 8A and 8B are schematic views illustrating aspects of signal processing in the IVUS imaging system.

As shown in FIG. 8A, ultrasound echo data (1,024 lines) needed to form one tomographic image of the blood vessel are acquired from every rotation of the ultrasonic transducer 401*b* (in the example of FIG. 8A, ultrasound echo data (801-806) needed to form six tomographic images (i.e., six frames as moving image) are acquired from six rotations of the ultrasonic transducer 401*b*).

The ultrasound echo data acquired from the respective rotations are stored in the mass storage unit 601 to permit their subsequent reproduction. In addition, portions of the ultrasound echo data acquired from every predetermined number of rotations are extracted to produce one frame of ultrasound echo data, which is displayed in real time. In the example of FIG. 8A, the ultrasound echo data for 0 degree to 120 degrees are extracted from the ultrasound echo data (801) acquired from the first rotation, the ultrasound echo data for 120 degrees to 240 degrees are extracted from the ultrasound echo data (802) acquired from the second rotation, and the ultrasound echo data for 240 degree to 360 degrees are extracted from the ultrasound echo data (803) acquired from the third rotation. These extracted ultrasound echo data are combined to produce one frame of ultrasound echo data (811).

Figure 8B:
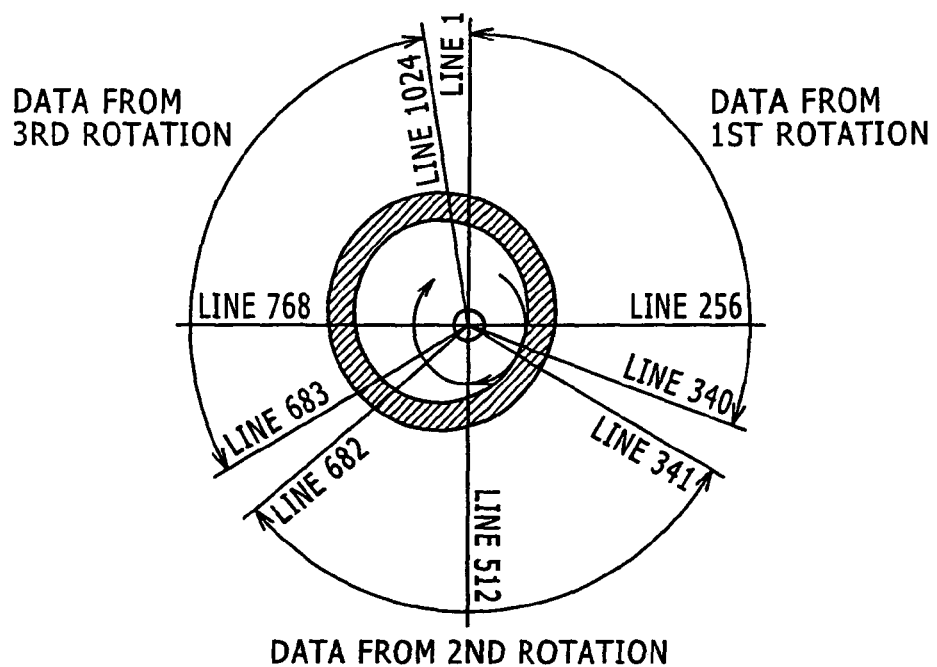

FIG. 8B diagrammatically illustrates the breakdowns of the one frame of ultrasound echo data (811) produced as described above. As shown in the figure, the ultrasound echo data (811) consist of lines 1 to 340 of ultrasound echo data from the first rotation, lines 341 to 682 of ultrasound echo data from the second rotation, and lines 683 to 1024 of ultrasound echo data from the third rotation. The produced ultrasound echo data are displayed in real time. Based on the ultrasound echo data acquired from the fourth rotation to the sixth rotation, another one frame of ultrasound echo data (812) are similarly produced and displayed in real time.

Each of the embodiments of FIG. 8A and FIG. 8B displays the frame data for a one-third part of the original ultrasound echo data.

As described above, even when the radial scanning by the ultrasonic transducer 401*b* is made faster than the normal frame rate of video signals (30 fps) to increase the number of tomographic images formable per unit time, tomographic images can still be formed at intervals commensurate with the frame rate of video signals by extracting portions of ultrasound echo data acquired from every predetermined plural number of rotations and combining them to form one frame of ultrasound echo data. As a result, a real-time display becomes feasible.

It is to be noted that in parallel with the above-described extraction of ultrasound echo data and the subsequent formation of tomographic images, the entire ultrasound echo data acquired from the respective rotations as mentioned above are stored in the mass storage unit 601 without extracting process. It is, therefore, possible to display all the ultrasound echo data later by reading the entire ultrasound echo data stored in the mass storage unit 601. As has been described above, the IVUS imaging system 100 can selectively perform a display of all data and a real-time display of extracted data even when the radial scanning by the ultrasonic transducer 401*b* is made faster. In addition, when all data is used for the display, the displayed moving image serves as slow motion since the number of frames acquired in unit time is more than the number of frames in real time by the frame rate of a video signal.

6.2 Processing at the Individual Units to Realize the Above-Described Signal Processing Set forth below is a description about the processing at the individual units in the signal processor 225 to realize the above-described signal processing. The following description is based on the assumption that the number of lines per rotation is 1,024, though as noted above this number of lines per rotation can be varied.

6.2.1 Processing at the Control Unit 607

Operational aspects of the control unit 607 upon performing a real-time display during an intravascular ultrasound diagnosis are shown by way of the flowchart in FIG. 9. In step S901, a frame rate of radial scanning and a frame rate of video signals are read. In step S902, the ratio ($\alpha$) of the frame rate of radial scanning to the frame rate of video signals so read is calculated.

In step S903, the ratio ($\alpha$) calculated in step S902 is transmitted to the signal extractor 602.

6.2.2 Processing at the Signal Extractor 602

Figure 10:
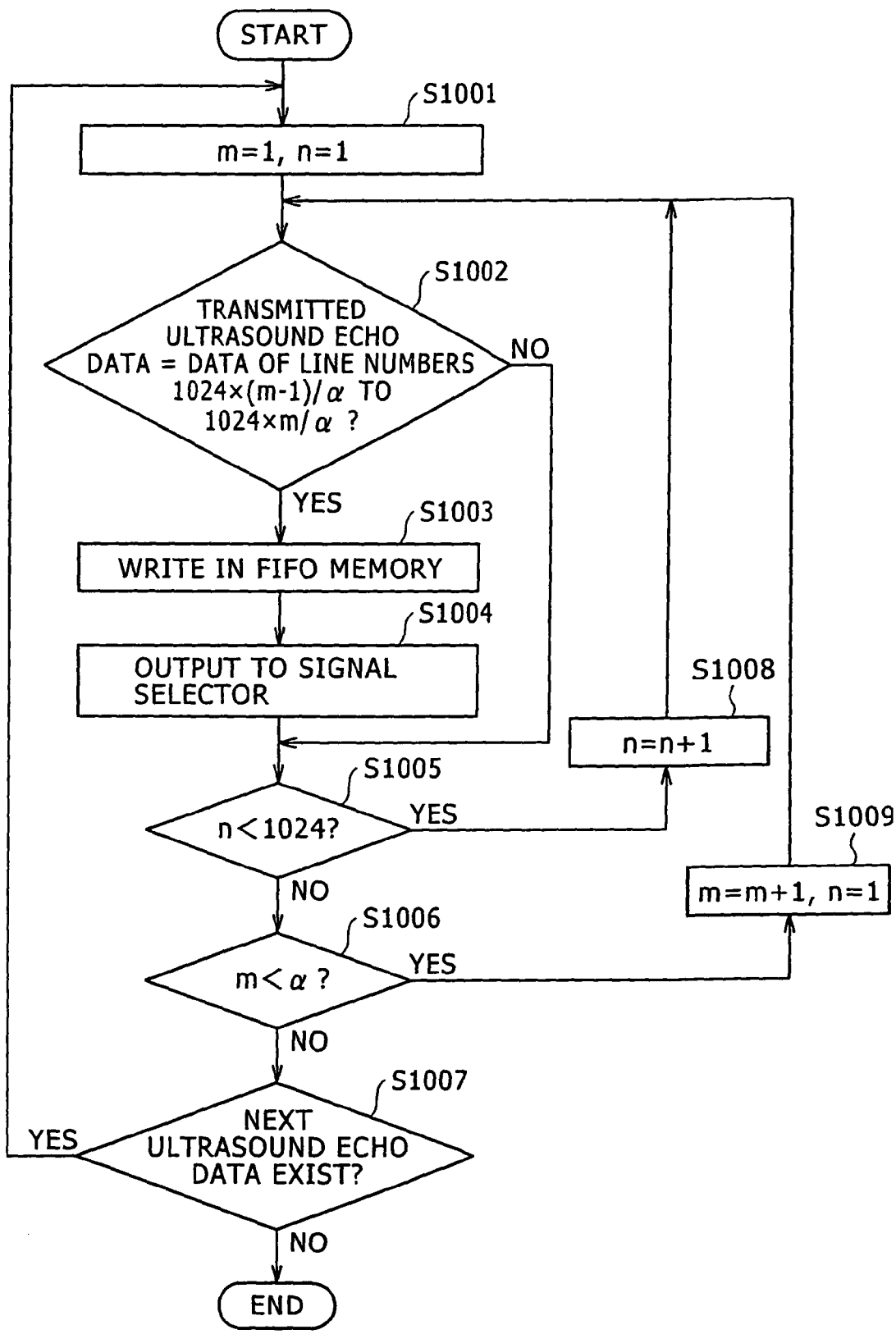
FIG. 10 is a flow chart showing operational aspects of a signal extractor upon conducting a real-time display in an intravascular ultrasound diagnosis.

Operational aspects of the signal extractor 602 upon performing a real-time display during an intravascular ultrasound diagnosis are shown by way of the flowchart in FIG. 10. In step S1001, count values m, n are set at 1, respectively, as initial values. The count value m is a parameter for counting the number of rotations of the ultrasonic transducer unit 401. The count value n, on the other hand, is a parameter for controlling the line number of ultrasound echo data.

In step S1002, a determination is made as to whether or not the line number of ultrasound echo data (line number=n) transmitted from the A/D converter 224 satisfies the conditions of the following formulas (Formula 1, Formula 2):

$$1024 \times (m-1)/\alpha \leq n \quad \text{(Formula 1)}$$

$$1024 \times m/\alpha > n \quad \text{(Formula 2)}$$

If the line number is determined to satisfy the conditions of Formula 1 and Formula 2 in step S11002, the process advances to step S1003 in which the ultrasound echo data (line number=n) are written in the FIFO memory. The process then advances to step S1004 in which the ultrasound echo data are read, and are outputted at a predetermined timing to the signal selector 603. Subsequently, the process advances to step S1005. In this case, the ultrasound echo data will be used for a real-time display.

If the line number is not determined to satisfy the conditions of the Formula 1 and Formula 2 in step S1002, on the other hand, the FIFO memory is write-inhibited and the process advances directly to step S1005. In this case, the ultrasound echo data will not be used for a real-time display.

In step S1005, a determination is made as to whether or not the count value n is smaller than 1,024. If the count value n is determined to be smaller than 1,024, the process advances to step S1008 and, after the count value n is incremented, the process returns to step S1002. If the count value n is determined to be equal to 1,024, on the other hand, the process advances to step S1006.

In step S1006, a determination is made as to whether or not the count value m is smaller than $\alpha$. If the count value m is determined to be smaller than $\alpha$, the process advances to step S1009 in which the count value m is incremented and 1 is inputted as the count value n.

If the count value m is determined to be equal to a in step S1006, on the other hand, the process advances to step S1007. In step S1007, a determination is made as to whether or not next ultrasound echo data exist. If next ultrasound echo data are determined to exist, the process returns to step S1001. If no next ultrasound echo data are determined to exist, the processing is ended.

6.2.3 Example

Set forth below is a description of an example involving the flow charts shown in FIGS. 9 and 10. It is assumed that the frame rate of video signals is 30 fps and the frame rate of radial scanning is 90 fps (the rotating speed of the driveshaft is 5,400 rpm). In this case, the ratio of the frame rate of radial scanning to the frame rate of video signals is 3:1 so that following the flow chart of FIG. 9, $\alpha$=3 is calculated at the control unit 607.

At the signal extractor 602, ultrasound echo data are, therefore, extracted over 120 degrees per rotation from the ultrasound echo data in three rotations. More specifically, among the inputted ultrasound echo data, lines 1 to 340 are extracted from the first rotation, lines 341 to 682 are extracted from the second rotation, and lines 683 to 1024 are extracted from the third rotation.

The IVUS imaging system described herein is able to form tomographic images at intervals commensurate with the frame rate of video signals by extracting ultrasound echo data on the basis of the ratio of the frame rate of radial screening to the frame rate of video signals.

As a result, a real-time display can be performed irrespective of the frame rate of video signals even when the radial scanning by an ultrasonic transducer is made faster.

Second Embodiment

In the above-described first embodiment, each tomographic image is formed by extracting portions of ultrasound echo data from every three rotations and combining them together. However, the apparatus and method here are not limited specifically to such an embodiment. For example, ultrasound echo data from every predetermined $n^{th}$ (n: 1, 2, 3, . . . ) rotation may be extracted, as are, based on the ratio of the frame rate of radial scanning to the frame rate of video signals. The description which follows describes signal processing in a so-constructed IVUS imaging system according to a second embodiment.

Figure 11:
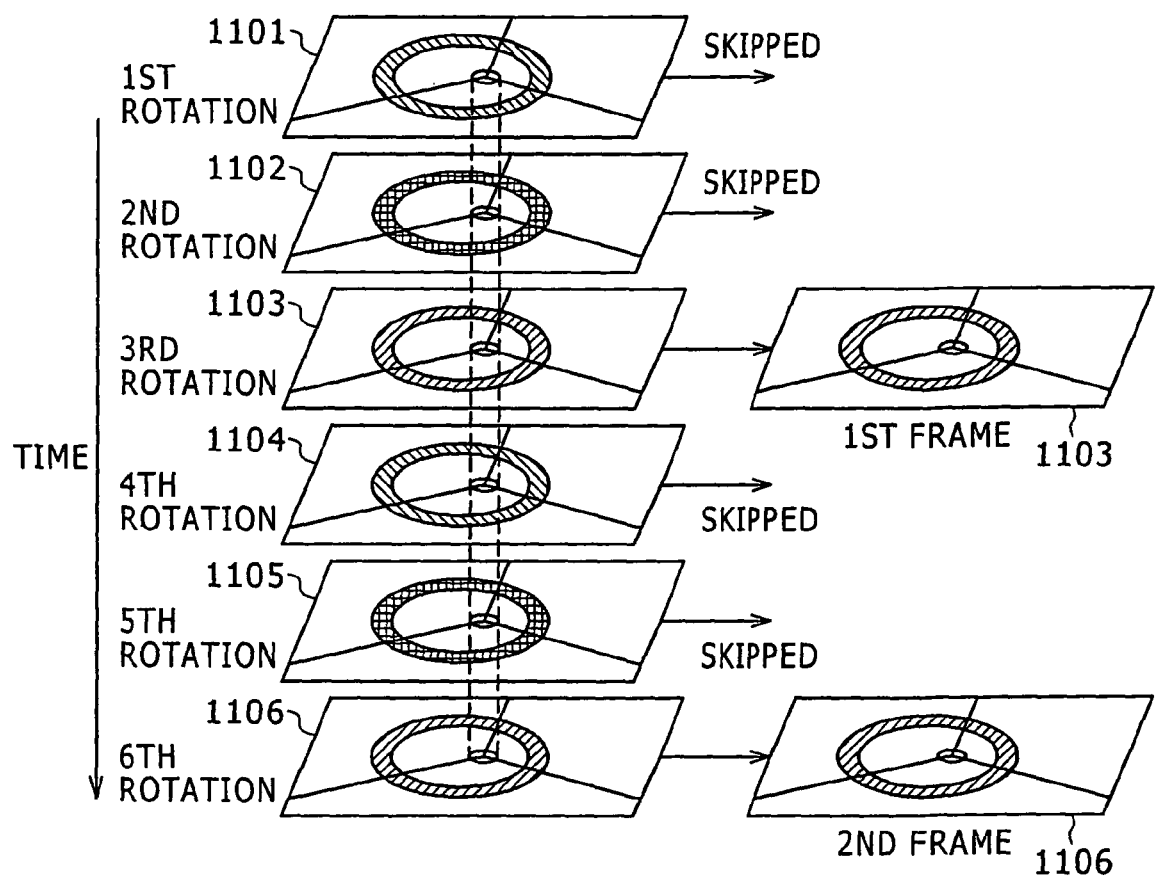
FIG. 11 is a schematic view illustrating aspects of signal processing in an IVUS imaging system according to a second embodiment of the present invention.

1. Signal Processing During an Intravascular Ultrasound Diagnosis 1.1 Outline of Signal Processing Signal processing in the IVUS imaging system 100 during an intravascular ultrasound diagnosis according to the second embodiment is illustrated in FIG. 11. The ultrasonic transducer is rotating at a speed 3 times the normal video rate (30 fps=1,800 rpm).

As shown in FIG. 11, ultrasound echo data (1,024 lines) needed to form one tomographic image of a blood vessel are acquired from every rotation of an ultrasonic transducer 401b (in the example of FIG. 11, ultrasound echo data (1101-1106) needed to form six tomographic images are acquired from six rotations of the ultrasonic transducer).

The ultrasound echo data acquired from the respective rotations are stored in a mass storage unit to permit their reproduction after the measurement. In addition, the ultrasound echo data acquired from every predetermined $n^{th}$ (n: 1, 2, 3, . . . ) rotation are extracted, and are displayed in real time. In the example of FIG. 11, the ultrasound echo data (1103) from the third rotation are extracted, and are used for a real-time display. Similarly, the ultrasound echo data (1106) from the sixth rotation are extracted, and are used for a real-time display.

As has been described above, tomographic images can be formed at intervals commensurate with the frame rate of video signals by decimating some of the ultrasound echo data (not using some of the ultrasound echo data) and using the remaining ultrasound echo data for a real-time display even when the radial scanning by an ultrasonic transducer 401b is made faster to increase the number of tomographic images formable per unit time. As a result, a real-time movie display becomes feasible.

1.2 Processing at Individual Units to Realize the Above-Described Signal Processing The processing at individual units in a signal processor 225 to realize the above-described signal processing is as follows. The following description is set forth based on the assumption that the number of lines per rotation is 1,024.

1.2.1 Processing at a Control Unit 607

The processing at the control unit 607 is similar to that described above in connection with FIG. 9 and so a detailed description is not repeated again.

1.2.2 Processing at a Signal Extractor 602

Figure 12:
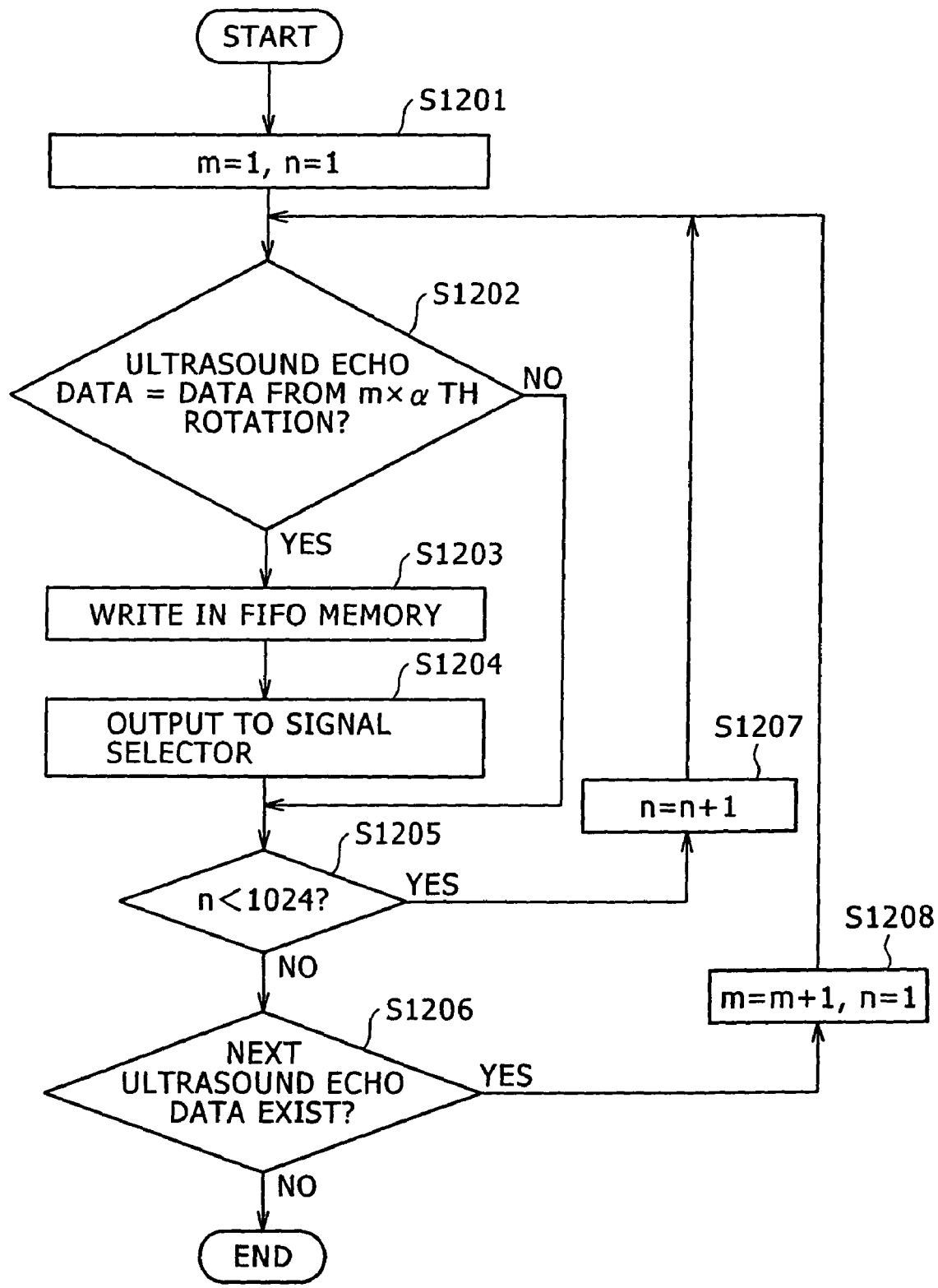
FIG. 12 is a flow chart showing operational aspects of a signal extractor upon conducting a real-time display in an intravascular ultrasound diagnosis.

FIG. 12 is a flow chart showing processing at the signal extractor 602 upon performing a real-time display during an intravascular ultrasound diagnosis. In step S1201, count values m, n are set at 1, respectively, as initial values. The count values m, n are similar to the parameters described above in the first embodiment. In step S1202, a determination is made as to whether or not the ultrasound echo data of line number=n from an A/D converter 224 are the ultrasound echo data of the m×$\alpha^{th}$ rotation.

If the ultrasound echo data of line number=n are determined to be the ultrasound echo data of the m×$\alpha^{th}$ rotation in step S1202, the process advances to step S1203 in which the ultrasound echo data (line number=n) are written in an FIFO memory. The process then advances to step S1204 in which the ultrasound echo data are extracted and, after they are outputted at a predetermined timing to a signal selector 603, the process advances to step 1205. In this case, the ultrasound echo data will be used for a real-time display.

If the ultrasound echo data of line number=n are not determined to be the ultrasound echo data of the m×$\alpha^{th}$ rotation in step S1203, on the other hand, the FIFO memory is write-disabled and the process advances directly to step S1205. In this case, the ultrasound echo data will not be used for a real-time display.

In step S1205, a determination is made as to whether or not the count value n is smaller than 1,024. If the count value n is determined to be smaller than 1,024, the process advances to step S1207 and, after the count value n is incremented, the process returns to step S1202. If the count value n is determined to be equal to 1,024, on the other hand, the process advances to step S1206.

In step S1206, a determination is made as to whether next ultrasound echo data exist. If next ultrasound echo data are determined to exist, the process advances to step S1208. In step S1208, the count value m is incremented, and subsequent to setting of 1 as the count value n, the process returns to step S1202.

If no next ultrasound echo data are determined to exist in step S1206, on the other hand, the processing is ended.

1.2.3 Example

Set forth below is a description of an example involving the flow chart shown in FIG. 12. It is assumed that the frame rate of video signals is 30 fps and the frame rate of radial scanning is 90 fps (5,400 rpm). In this case, the ratio of the frame rate of radial scanning to the frame rate of video signals is 3:1 so that following the flow chart of FIG. 9, $\alpha=3$ is calculated at the control unit.

Accordingly, the ultrasound echo data acquired during the single rotations of the $3^{rd}$, $6^{th}$, $9^{th}$, . . . rotations are extracted at the signal extractor. This gives that ultrasound echo data are skipped in frame units.

As evident from the above description, the IVUS imaging system according to this embodiment can form tomographic images at intervals commensurate with the frame rate of video signals by extracting ultrasound echo data in frame units on the basis of the ratio of the frame rate of radial screening to the frame rate of video signals.

As a result, a real-time display can be performed irrespective of the frame rate of video signals even when the radial scanning by an ultrasonic transducer is made faster.

Third Embodiment

Each of the above-described first and second embodiments involves processing at the signal processor when the radial scanning by the ultrasonic transducer is made faster in the IVUS imaging system. However, the disclosed system and method are not limited specifically to IVUS imaging systems. Indeed, the disclosure herein is also applicable to other image diagnostic systems. The description which follows describes application of the disclosed subject matter to an optical coherence tomography (OCT) imaging system.

1. Measurement Principle of OCT Imaging System

For background purposes, set forth below is a general description of the diagnostic principle of the OCT imaging system. Because light is electromagnetic radiation, it generally has the property that beams of light interfere with each other when they are superimposed. The interference property defining whether light interferes readily or hardly is called "coherence." In general OCT imaging systems, low-coherence light (i.e., short-coherence light) of low interference property is used.

Referring to FIG. 13A, when time is plotted along the abscissa and electric field is plotted along the ordinate, low-coherence light becomes random signals as indicated at 1301 and 1302. Individual peaks in the figure are called "wave trains", and have their own, mutually-independent phases and amplitudes. When the same wave trains (1301 and 1302) overlap with each other as in FIG. 13A, the wave trains interfere with each other to intensify each other as represented at 1303. On the other hand, when there is a slight delay in time between wave trains (1304 and 1305 in FIG. 13B), the wave trains cancel each other so that no interference is observed as represented at 1306 in FIG. 13B.

Figure 14:
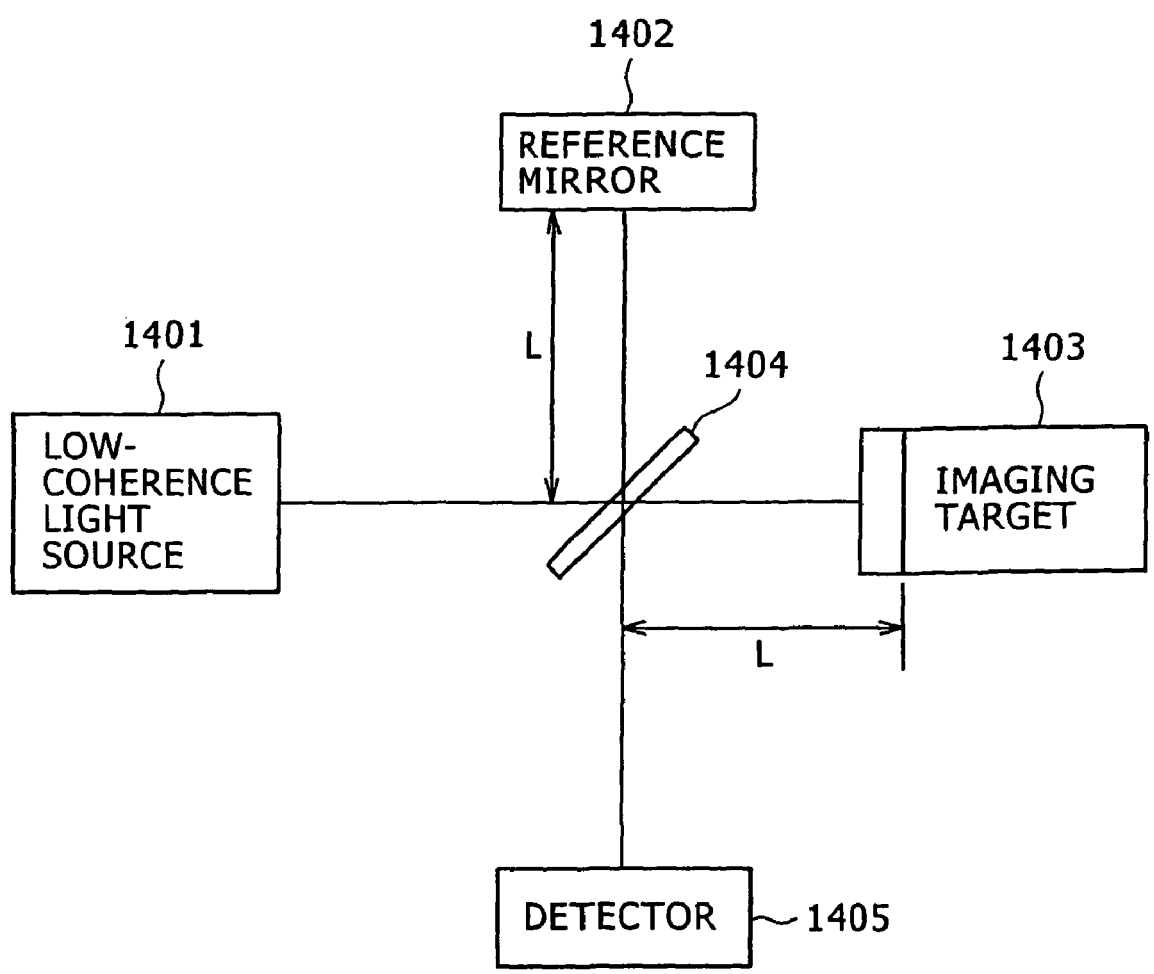
FIG. 14 is a block diagram schematically illustrating the basic principle of the OCT imaging system.

The OCT imaging system makes use of these properties, and the basic principle of the system is illustrated in FIG. 14. As illustrated, light emitted from a low-coherence light source 1401 is split into a reference path and a sampling path at a beam splitter 1404. One of the resulting light beams which is split into the reference path is then directed toward a reference mirror 1402 and another resulting light beam which is split into the sampling path is then directed toward an imaging target (i.e. blood vessel wall) 1403. At this time, reflected light returning from the imaging target includes light reflected on the surface of the imaging target, light reflected at shallow points in the imaging target, and light reflected at deep points in the imaging target.

As the incident light is low-coherence light, the reflected light on which interference can be observed is, however, only the reflected light from a reflection surface located at a position apart by a distance of $L+\Delta L/2$ from the beam splitter 1404, where L represents the distance from the beam splitter 1404 to the reference mirror 1402 and $\Delta L$ represents a coherence length.

By changing the distance from the beam splitter 1404 to the reference mirror 1402, it is possible to selectively detect at a detector 1405 only reflected light from a reflection surface, which corresponds to the thus-changed distance, in the imaging target. A tomographic image can then be constructed by visualizing internal structural information of the imaging target on the basis of the intensities of reflected light beams corresponding to such respective distances.

2. General Overall Construction of OCT Imaging System

The general overall of the OCT imaging system is similar to that of the IVUS imaging system described above and shown in FIG. 1, and so a detailed description of the construction of the OCT imaging system is not repeated.

3. Aspects and Features of OCT Imaging System

Figure 15:
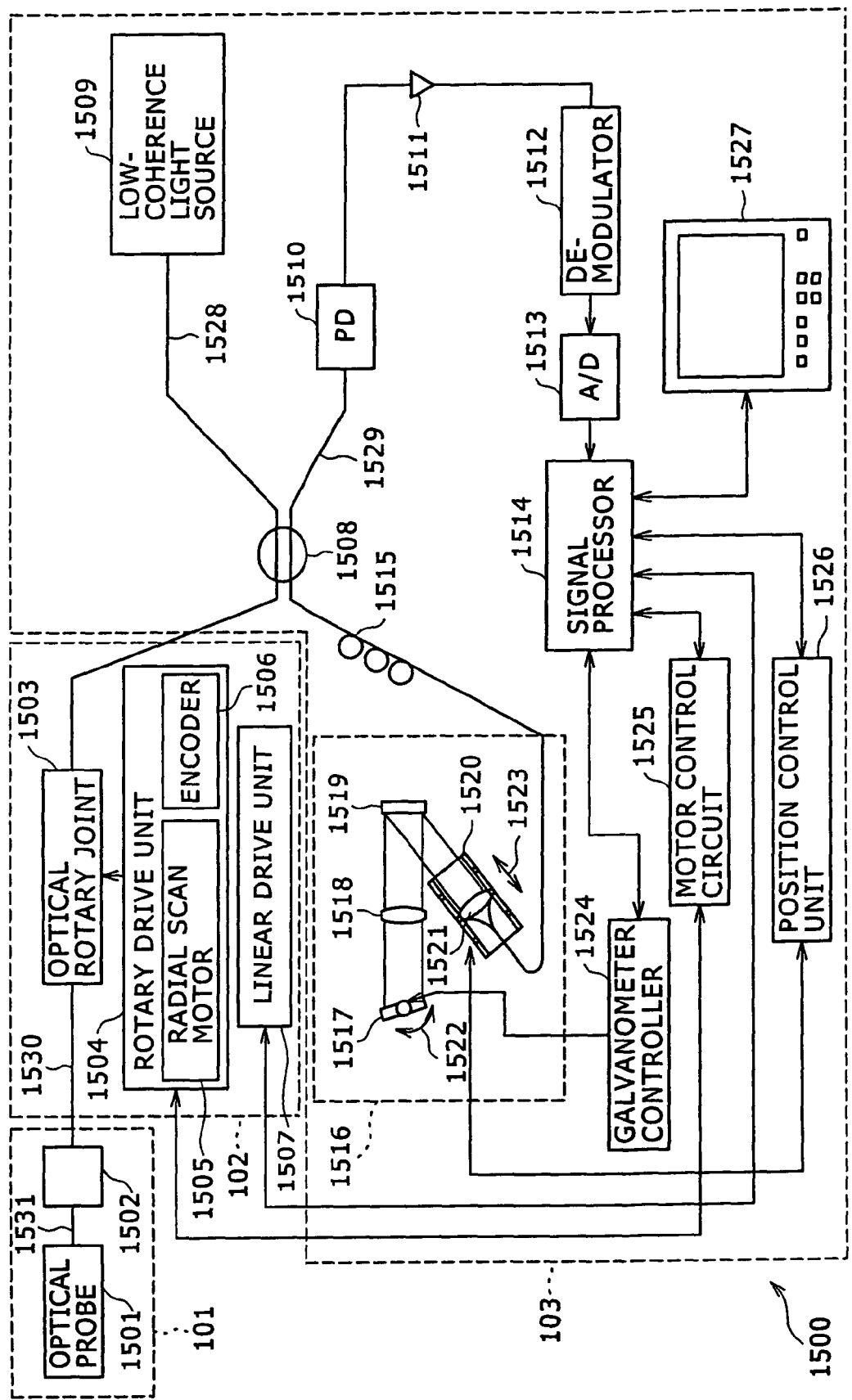
FIG. 15 is a block diagram schematically illustrating features of the OCT imaging system.

FIG. 15 illustrates features and aspects associated with the OCT imaging system (i.e., image diagnostic system) 1500 according to this illustrated and disclosed embodiment. The system includes a low-coherence light source 1509 such as a light emitting diode of ultra-high intensity. The low-coherence light source 1509 outputs low-coherence light having a wavelength around 1,310 nm, and the outputted low-coherence light shows interference property only in such a short distance range that its coherence length approximately ranges from several micrometers to over ten of micrometers.

When the light is split into two and the resulting beams of light are combined back, the combined light is, therefore, detected as coherent light when the difference between the two optical path lengths from the splitting point to the combining point falls within a short distance range around 17 μm, but no coherent light is detected when the difference in optical path length is greater than the above-described range.

The light from the low-coherence light source 1509 impinges on a proximal end face of a first single mode fiber 1528, and is transmitted toward its distal end face. At an optical coupler 1508 arranged midway along the first single mode fiber 1528, the first single mode fiber 1528 is optically coupled with a second single mode fiber 1529. Therefore, the light transmitted through the first single mode fiber 1528 is split into two by the optical coupler 1508 and the resulting two beams of light (i.e., the sample path and the reference path) are transmitted further.

On a more distal end side of the first single mode fiber 1528 than the optical coupler 1508, an optical rotary joint 1503 is arranged to connect a non-rotatable block and a rotatable block with each other such that light can be transmitted.

Further, an optical-probe connector 1502 is detachably connected to a distal end of a third single mode fiber 1530 in the optical rotary joint 1503. Via the connector 1502, the light from the low-coherence light source 1509 is transmitted to a fourth single mode fiber 1531 which is inserted in an optical probe (i.e., catheter) 1501 and is rotationally drivable.

The transmitted light is irradiated from the distal end side of the optical probe 1501 toward a surrounding biotissue of a body cavity while performing radial scanning. A portion of reflected light scattered on a surface or interior of the biotissue is collected by the optical probe 1501, and returns toward the first single mode fiber 1528 through the reverse optical path. A portion of the thus-collected, reflected light is transferred by the optical coupler 1508 to the side of the second single mode fiber 1529, and is introduced into a photodetector (for example, photodiode 1510) from an end of the second single mode fiber 1529. The rotatable block side of the optical rotary joint 1503 is rotationally driven by a radial scan motor 1505 of a rotary drive unit 1504. Further, rotation angles of the radial scan motor 1505 are detected by an encoder 1506. The optical rotary joint 1503 is provided with a linear drive unit 1507 which, based on an instruction from a signal processor 1514, controls a movement of the catheter section 101 in the direction of its insertion.

On the more distal end side of the second single mode fiber 1529 than the optical coupler 1508, an optical path length (OPL) varying mechanism 1516 is arranged to vary the optical path length of reference light.

This OPL varying mechanism 1516 is provided with a first OPL varying means for varying the optical path length, which corresponds to the examinable range in the direction of the depth of the biotissue, at high speed and also with a second OPL varying means for varying the optical path length by a length equivalent to a variation in the length of a new optical probe to absorb the variation when the new optical probe is used as a replacement (so generally intravascular probes are disposable for infection prevention).

Opposing the distal end of the second single mode fiber 1529, a grating (diffraction grating) 1519 is arranged via a collimator lens 1521 which is mounted together with the distal end of the second single mode fiber 1529 on a single axis stage 1520 and is movable in the direction indicated by arrow 1523. Further, a galvanometer mirror 1517 which is rotatable over small angles is mounted as the first OPL varying means via the grating 1519 and an associated lens 1518. This galvanometer mirror 1517 is rotated at high speed in the direction of arrow 1522 by a galvanometer controller 1524.

The galvanometer mirror 1517 serves to reflect light by its mirror, and functions as a reference mirror. The galvanometer mirror 1517 is constructed such that its mirror mounted on a movable part of its galvanometer is rotated at high speed by applying an a.c. drive signal to the galvanometer.

Described more specifically, by applying a drive signal to the galvanometer from the galvanometer controller 1524 and rotating the galvanometer at high speed in the direction of arrow 1522 with the drive signal, the optical path length of reference light is varied at high speed by an optical path length equivalent to an examinable range in the direction of the depth of the biotissue. A single cycle of variations in optical path length (single scanning) becomes a cycle that produces interference light data for a single line (in line unit).

On the other hand, the single axis stage 1520 forms the second OPL varying means having a variable OPL range just enough to absorb a variation in the optical path length of a new optical probe when the optical probe 1501 is replaced by the new (i.e., another) optical probe. In addition, the single axis stage 1520 is also able to function as an adjustment means for adjusting an offset. Even when the distal end of the optical probe 1501 is not in close contact with a surface of the biotissue, for example, the optical probe can still be set in such a state as interfering from a position on the surface of the biotissue by slightly varying the optical path length with the single axis stage 1520.

The light varied in the optical path length by the OPL varying mechanism 1516 is combined with the light, which has escaped from the side of the first single mode fiber 1528, at the optical coupler 1508 arranged midway along the second single mode fiber 1529, and the combined light is received at the photodiode 1510.

The light received at the photodiode 1510 is photoelectrically converted, amplified by an amplifier 1511, and then inputted into a demodulator 1512. At the demodulator 1512, demodulation processing is performed to extract only the signal portion of the interfered light, and the output of the demodulator 1512 is inputted into an A/D converter 1513.

At the A/D converter 1513, interference light signals are sampled as much as for 200 points to produce digital data (interference data) for one line. The sampling frequency is a value obtained by dividing with 200 the time required for a single scan of the optical path length.

The interference light data in the line unit, which have been produced at the A/D converter 1513, are inputted into the signal processor 1514. At this signal processor 1514, the interference light data in the direction of the depth are converted into video signals to constitute tomographic images at respective positions in the blood vessel. These tomographic images are then outputted at a predetermined frame rate to an LCD monitor 1527.

The signal processor 1514 is connected with a position control unit 1526. The signal processor 1514 performs control of the position of the single axis stage 1520 via the position control unit 1526. In addition, the signal processor 1514 is also connected with a motor control circuit 1525 to control rotational drive by the radial scan motor 1505.

Further, the signal processor 1514 is also connected with the galvanometer controller 1524 which controls the scanning of the optical path length of the reference mirror (galvanometer mirror). The galvanometer controller 1524 outputs a drive signal to the signal processor 1514, and based on this drive signal, the motor control circuit 1525 is synchronized with the galvanometer controller 1524.

4. Construction of Catheter Section

Figure 16:
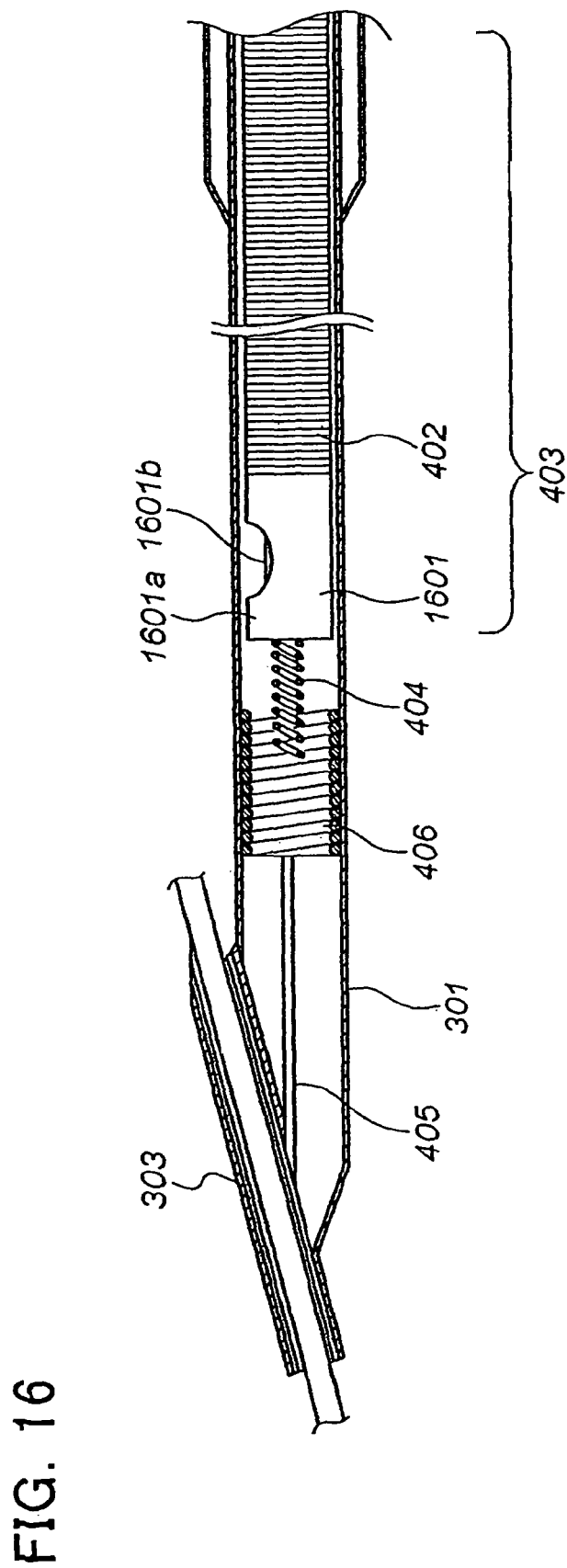
FIG. 16 is a cross-sectional view of the distal end portion of a catheter section in the OCT imaging system.

The overall construction of the catheter section 101 in the OCT imaging system is the same as the overall construction of the catheter section in the IVUS imaging system described above and so a detailed description of such overall construction is not repeated here. With reference to FIG. 16, the following describes differences associated with the construction of the distal end portion of the catheter section 101 in the OCT imaging system 1500.

An optical probe 1601 which irradiates/receives low-coherence light is arranged within the lumen of the catheter sheath 301. The optical probe 1601 is provided with a prism or mirror 1601b to perform lateral irradiation. The optical probe 1601 includes the prism or mirror 1601b and a housing 1601a in which is held the prism or mirror 1601b. The optical probe 1601 irradiates the low-coherence light toward a surrounding biotissue of a body cavity from the prism or mirror 1601b, and receives the reflected light from the surrounding biotissue of the body cavity through the prism or mirror 1601b.

An optical fiber is disposed through the drive shaft 402, and extends from the housing 1601a to the connector 1502. As the advance injection of physiological saline (priming work) is not absolutely needed in the OCT imaging system according to this embodiment, the priming discharge channel 405 formed at the boundary portion between the distal end portion of the catheter sheath 301 and the guidewire lumen 303 in the IVUS imaging system described above may be omitted.

5. Features of the Signal Processor

Features associated with the signal processor 1514 in the OCT imaging system 1500 are illustrated in FIG. 17. The signal processor includes a control unit 1704 that systematically controls the OCT imaging system 1500 in its entirety. The signal processor also includes a mass storage unit 1701 which is composed of a hard disk, semiconductor memory or the like. At the mass storage unit 1701, all interference light data transmitted from the photodiode 1510 via the demodulator 1512 and A/D converter 1513 are successively received in cycle units of variations in optical path length (i.e., scanning line units), and are stored.

The interference light data stored in the mass storage unit 1701 are read in accordance with a frame rate of video signals as needed (based on instructions from the control unit 1706), and are then fed to a signal selector 1703.

The capacity of the mass storage unit 1701 is determined depending on how many frames of data are to be acquired by radial scanning. When a 150-mm blood vessel is subjected to radial scanning at a pitch of 0.5 mm, for example, 300 frames of data are acquired. If each frame consists of 16-bit data of 1,024 lines×200 samples, the total data size becomes 118 Mbytes. In this case, a semiconductor memory or hard disk of 1 Gbytes or greater can be chosen as the mass storage unit 1701.

A signal extractor 1702 is equipped with a function to selectively extract predetermined interference light data from the interference light data transmitted from the A/D converter 1513. The signal extractor 1702 can be composed of an FIFO memory with a write inhibit function. In synchronization with each output pulse from the encoder 1506, the write enable/disable status of the FIFO memory is controlled. Only when the FIFO memory is writable, inputted interference light data are written in the FIFO memory.

More specifically, the FIFO memory is made writable in the cycle unit of variations in light path length (line unit) so that interference light data corresponding to radial scanning for one frame can be constructed. If unnecessary interference light data are inputted, the FIFO memory is write-disabled. Reading from the FIFO memory is performed in synchronization with a timing of subsequent processing, and the thus-read interference light data are outputted to the signal selector 1703. It is to be noted that details of an extraction method of interference light data will be described subsequently herein.

When the signal selector 1703 receives from the control unit 1706 an instruction to the effect that the interference light data stored in the mass storage unit 1701 are to be read, the signal selector 1703 reads the interference light data from the mass storage unit 1701, and transmits them to a signal post-processor 1704. When the signal selector 1703 receives from the control unit 1706 an instruction of a real-time moving image display, on the other hand, the signal selector 1703 reads the interference light data extracted at the signal extractor 1702, and transmits them to the signal post-processor 1704.

The signal post-processor 1704 performs processing such as frame correlation, gamma correction, contrast adjustment and sharpness filtering on the interference light data transmitted from the signal selector 1703, and outputs the resulting data to an image construction unit 1705.

At the image construction unit 1705, streams of interference light data in scanning units along the optical path length by low-coherence light (line units) are converted into video signals. Based on the video signals, tomographic images to be displayed on the LCD monitor 1527 are constructed.

As a result, when the signal selector 1703 receives from the control unit 1706 an instruction to the effect that the interference light data stored in the mass storage unit 1701 are to be read, the tomographic images formed based on the interference light data stored in the mass storage unit 1701 are displayed on the LCD monitor 1527. When an instruction for a real-time display of images is received, on the other hand, tomographic images formed based on the interference light data extracted at the signal extractor 1702 are displayed corresponding to the radial scanning by an optical probe (i.e., catheter) 1601. In other words, control is effected such that the LCD monitor 1527 performs two types of tomographic image displays, one being a real-time display during radial scanning and the other a display after the radial scanning.

6. Processing During Optical Coherence Tomography 6.1 Outline of Processing

Figure 18A:
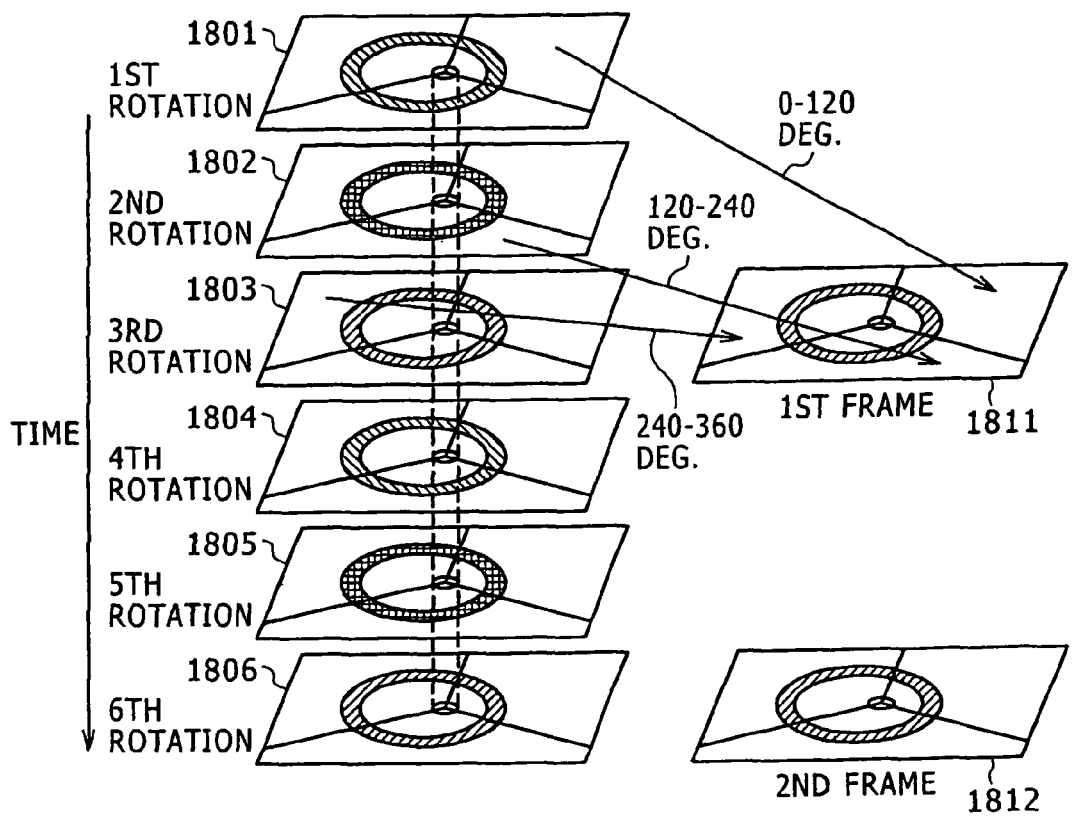
FIG. 18A and 18B are schematic views illustrating aspects of signal processing in the OCT imaging system.

Referring to FIGS. 18A and 19A, set forth below is a description of the signal processing in the OCT imaging system 1500 according to this embodiment during optical coherence tomography. As shown in FIG. 18A, interference light data (1,024 lines) needed to form one tomographic image of a blood vessel are acquired from every rotation of the optical probe 1501 (in the example of FIG. 18A, interference light data (1801-1806) needed to form six tomographic images are acquired from six rotations of the optical probe 1501).

The interference light data acquired from the respective rotations are stored in the mass storage unit 1701 to permit their reproduction after the measurement. In addition, portions of the interference light data acquired from every predetermined number of rotations are extracted to produce one frame of interference light data, which is displayed in real time. In the example of FIG. 18A, the interference light data for 0 degree to 120 degrees are extracted from the interference light data (1801) acquired from the first rotation, the interference light data for 120 degrees to 240 degrees are extracted from the interference light data (1802) acquired from the second rotation, and the interference light data for 240 degree to 360 degrees are extracted from the interference light data (1803) acquired from the third rotation. These extracted interference light data are combined to produce one frame of interference light data (1811).

Figure 18B:
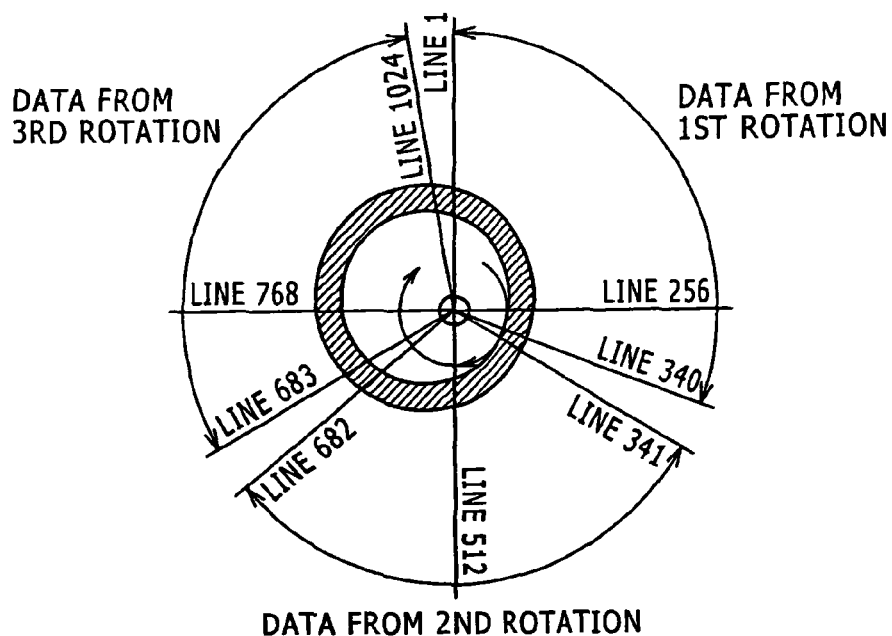

FIG. 18B diagrammatically illustrates the breakdown of the one frame of interference light data (1811) produced as described above. As shown, the interference light data (1811) consist of lines 1 to 340 of interference light data from the first rotation, lines 341 to 682 of interference light data from the second rotation, and lines 683 to 1024 of interference light data from the third rotation. The produced interference light data are displayed in real time.

Based on the interference light data acquired from the fourth rotation to the six rotation, another one frame of interference light data (1812 shown in FIG. 18A) are similarly produced and displayed in real time.

As described above, even when the radial scanning by the optical probe 1501 is made faster to increase the number of tomographic images formable per unit time, tomographic images can still be formed at intervals commensurate with the frame rate of video signals by extracting portions of interference light data acquired from every predetermined plural number of rotations and combining them to form one frame of interference light data. As a result, a real-time display becomes feasible.

Together with the above-described extraction of interference light data and the subsequent formation of tomographic images for real-time display, the interference light interference light data (line number=n) transmitted from the A/D converter 1513 satisfies the conditions of the following formulas (Formula 1, Formula 2):

$$1024 \times (m-1)/\alpha \leq n \quad \text{(Formula 1)}$$

$$1024 \times m/\alpha > n \quad \text{(Formula 2)}$$

If the line number is determined to satisfy the conditions of the Formula 1 and Formula 2 in step S2002, the process advances to step S2003, in which the interference light data (line number=n) are written in the FIFO memory. The process then advances to step S2004, in which the interference light data are extracted, and are outputted at a predetermined timing to the signal selector 1703. Subsequently, the process advances to step S2005. In this case, the interference light data will be used for a real-time display.

If it is determined in step S2002 that the line number does not satisfy the conditions of Formula 1 and Formula 2, on the other hand, the FIFO memory is write-inhibited and the process advances directly to step S2005. In this case, the interference light data will not be used for a real-time display.

In step S2005, a determination is made as to whether or not the count value n is smaller than 1,024. If the count value n is determined to be smaller than 1,024, the process advances to step S2008 and, after the count value n is incremented, the process returns to step S2002. If the count value n is determined to be equal to 1,024, on the other hand, the process advances to step S2006.

In step S2006, a determination is made as to whether or not the count value m is smaller than α. If the count value m is determined to be smaller than α, the process advances to step S2009, in which the count value m is incremented and 1 is inputted as the count value n. data acquired from the respective rotations as mentioned above are stored in the mass storage unit 1701. It is, therefore, possible to display all the interference light data later by reading all the interference light data stored in the mass storage unit 1701. As has been described above, the OCT imaging system 1500 can perform a display of all data in slow motion and a display of extracted data in real-time motion selectively, even when the radial scanning by the optical probe 1501 is made faster or increased.

6.2 Processing at the Individual Units to Realize the Above-Described Signal Processing The processing carried out at the individual units in the signal processor 1514 to achieve the above-described signal processing is described below. The following description is based on the assumption that the number of lines per rotation is 1,024, though as noted above this number of lines per rotation can be varied.

6.2.1 Processing at the Control Unit 1706

Figure 19:
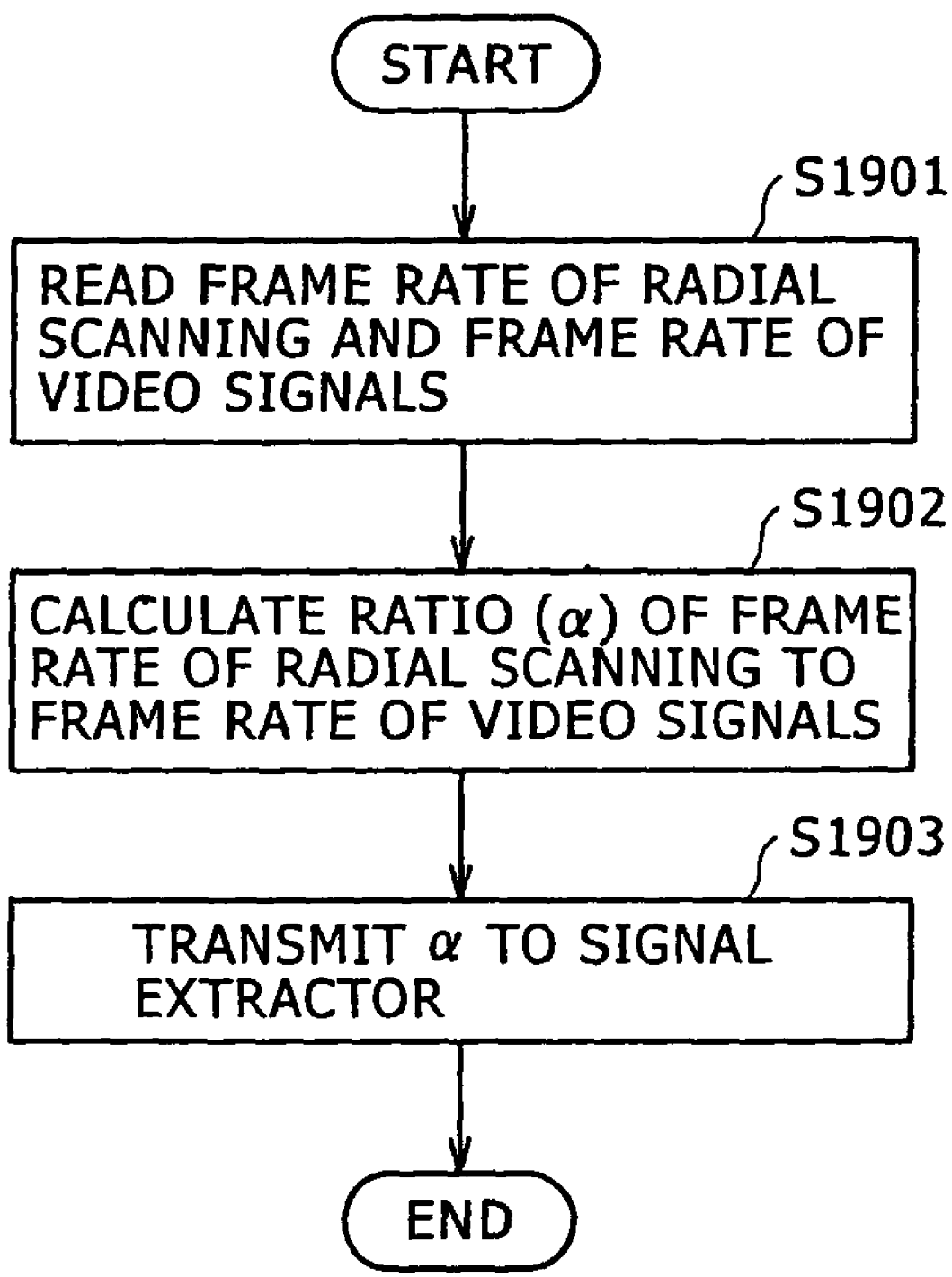
FIG. 19 is a flow chart showing operational aspects of a control unit upon conducting a real-time display in optical coherence tomography.

FIG. 19 is a flow chart showing operational aspects of the processing at the control unit 1706 upon performing a real-time display during intravascular optical coherence tomography. In step S1901, a frame rate of radial scanning and a frame rate of video signals are read. In step S1902, the ratio (α) of the frame rate of radial scanning to the frame rate of video signals so read is calculated. In step S1903, the ratio (a) calculated in step S1902 is transmitted to the signal extractor 1702.

6.2.2 Processing at the Signal Extractor 1702

Figure 20:
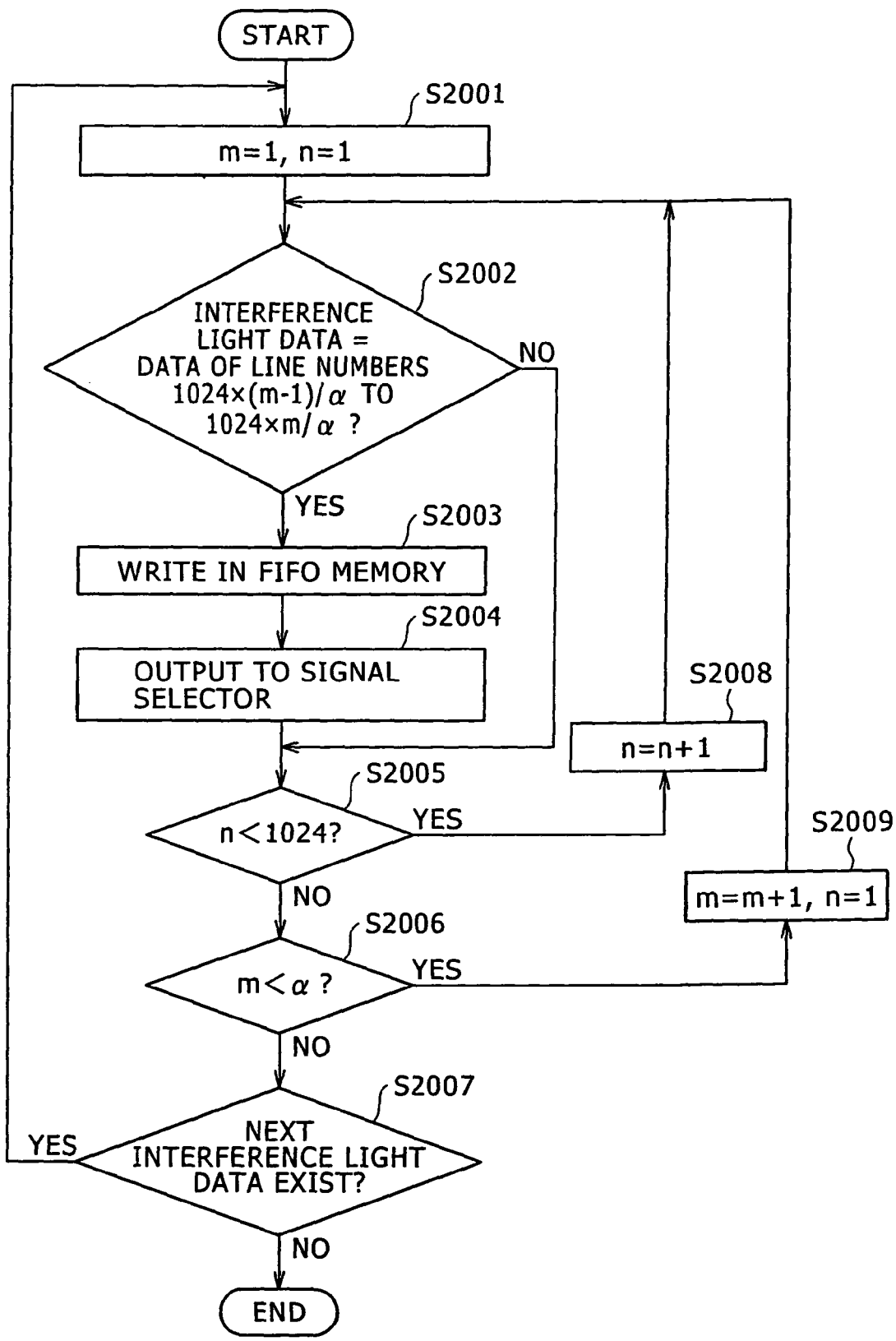
FIG. 20 is a flow chart showing operational aspects of a signal selector upon conducting a real-time display in optical coherence tomography.

FIG. 20 is a flow chart illustrating operational aspects of the processing at the signal extractor 1702 upon performing a real-time display during intravascular optical coherence tomography. In step S2001, count values m, n are set at 1, respectively, as initial values. The count value m is a parameter for counting the number of rotations of the optical probe 1501. The count value n, on the other hand, is a parameter for controlling the line number of interference light data.

In step S2002, a determination is made as to whether or not the line number of If the count value m is determined to be equal to α in step S2006, on the other hand, the process advances to step S2007. In step S2007, a determination is made as to whether or not next interference light data exist. If next interference light data are determined to exist, the process returns to step S2001. If no next interference light data are determined to exist, the processing is ended.

As evident from the above description, the OCT imaging system according to this embodiment can form tomographic images at intervals commensurate with the frame rate of video signals by extracting interference light data on the basis of the ratio of the frame rate of radial screening to the frame rate of video signals.

As a result, a real-time display can be performed irrespective of the frame rate of video signals even when the radial scanning by an optical probe is made faster.

This embodiment has been described in the context of the signal processing, which has been described above in the first embodiment, as applied to the OCT imaging system. However, the signal processing described above in the second embodiment, can also be applied to the OCT imaging system by replacing "ultrasound echo data" with "interference light data".

Fourth Embodiment

The third embodiment described above applies subject matter disclosed herein to an OCT imaging system. However, the subject matter at issue here is not specifically limited to OCT imaging systems, but can also be applied to OCT imaging systems making use of a wavelength swept light source. The following description describes application of the disclosed subject matter to an OCT imaging system making use of a wavelength swept light source.

1. Measurement Principle of OCT Imaging System Making Use of a Wavelength Swept Light Source Initially, a brief description is set forth of the measurement principle of the OCT imaging system making use of a wavelength swept light source. This OCT imaging system making use of a wavelength swept light source and the OCT imaging system described above as the third embodiment are basically the same in terms of the measurement principle as generally illustrated in FIGS. 13 and 14. Thus, the following description primarily discusses differences of this version of the OCT imaging system relative to the OCT imaging system described above as the third embodiment.

In this embodiment, it is primarily the light source that is different in measurement principle from the OCT imaging system described above as the third embodiment. First, these OCT imaging systems are thus different in coherence length. More specifically, a light source capable of emitting low-coherence light of from 10 μm to 20 μm or so in coherence length is used as the light source in the OCT imaging system described above as the third embodiment. On the other hand, a light source capable of emitting coherence light of from 4 mm to 10 mm or so in coherence length is used as a light source in the OCT imaging system making use of a wavelength swept light source.

One reason for the above-mentioned difference, the examinable range in the direction of the depth of a biotissue is dependent on the movable range of the reference mirror in the OCT imaging system described above as the third embodiment, but is dependent on the coherence length in the OCT imaging system making use of a wavelength swept light source. To encompass the entire range in the direction of the depth of a biotissue such as a blood vessel, a light source having a relatively long coherence length is used in the OCT imaging system making use of a wavelength swept light source.

Another difference in the light sources resides in that in the case of the OCT imaging system making use of a wavelength swept light source, light beams having different wavelengths are continuously irradiated.

In the OCT imaging system according to the third embodiment described above, the extraction of reflected light from individual points in the direction of the depth of the biotissue is achieved by movements of the reference mirror, and the resolution in the direction of the depth of the measurement target is dependent on the coherence length of irradiated light.

In the OCT imaging system making use of a wavelength swept light source, on the other hand, light is irradiated while continuously varying its wavelength and the intensities of reflected light from individual points in the direction of the depth of the biotissue are determined based on differences in the frequency component of interference light.

Taking the frequency (the inverse of the wavelength) of scanning light as a time function represented by Equation 1 below, the intensity of interference light can generally be expressed by a time function represented by Equation 2.

$$f(t) = f_\alpha + \Delta ft \quad \text{(Equation 1)}$$

$$I(t) = A + B \cos(C\Delta x(f_\alpha + \Delta ft)) \quad \text{(Equation 2)}$$

where Δx: optical path difference between the reference light and the target light,
Δf: the rate of a change in frequency in unit time, and
A, B, C: constants.

As indicated by Equation 2, the frequency component in the time-dependent change in the intensity I(t) of reference light is expressed by the optical path difference Δx and the rate Δf of a change in frequency by frequency scanning. Accordingly, the intensity of interference light for each optical path difference can be determined if the frequency component of the interference light is known.

As a consequence, the time required for acquiring signals for one line can be shortened, and further the imaging depth can be made greater.

Figure 21:
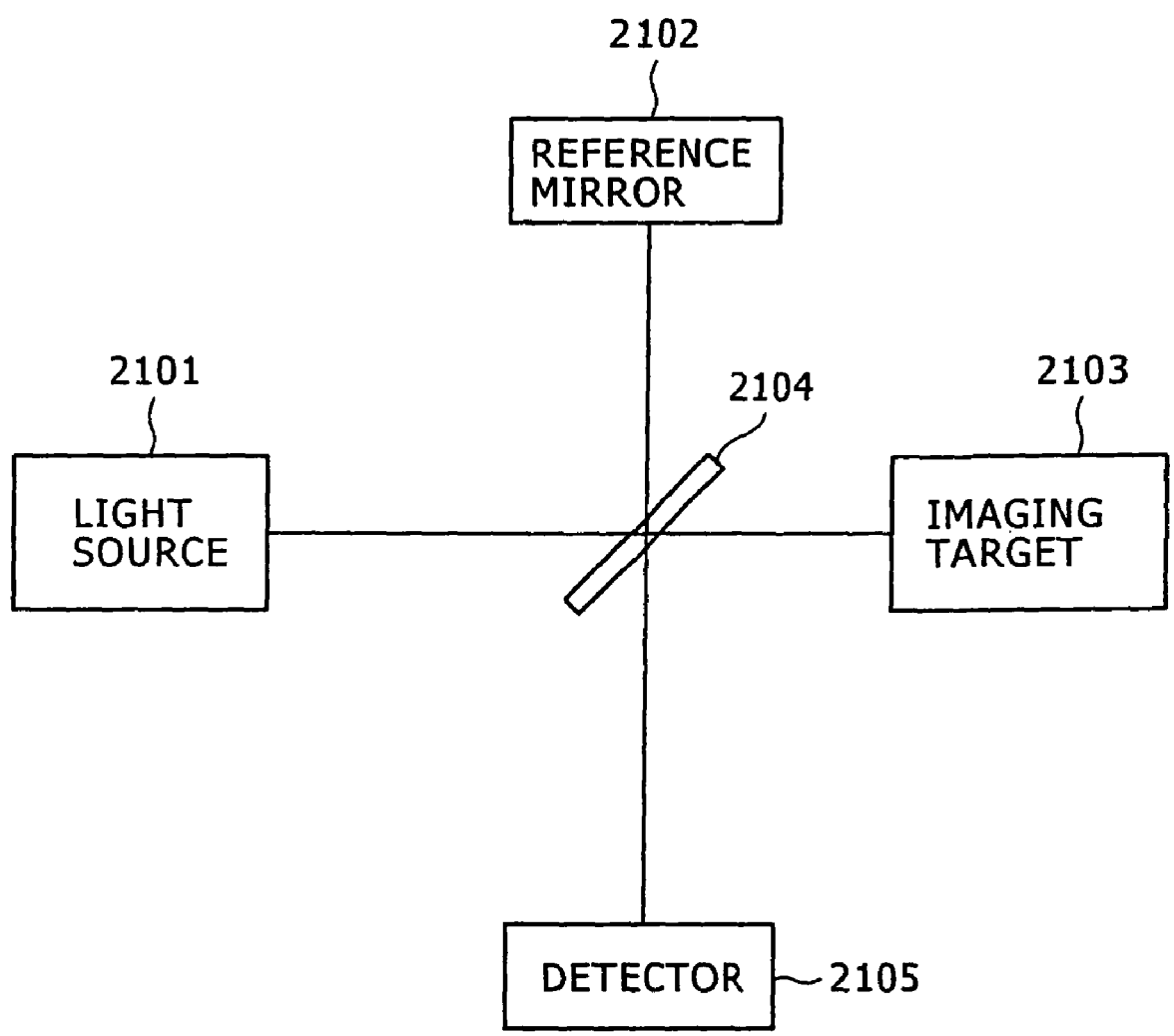
FIG. 21 is a block diagram schematically illustrating the basic principle of an OCT imaging system according to a fourth embodiment which makes use of a wavelength swept light source.

An example of the basic principle of an OCT imaging system making use of a wavelength swept light source is shown in FIG. 21 which depicts the light source 2101 as a swept laser.

Light beams, which have been successively outputted from the light source 2101 and have different wavelengths, are each split at a beam splitter 2104, and the thus-split light beams then travel toward a reference mirror 2102 and an imaging target 2103, respectively. At this time, reflected light which is returning from the side of the imaging target 2103 includes light reflected on the surface of the imaging target, light reflected at shallow points in the imaging target, and light reflected at deep points in the imaging target.

By subjecting observed reference light to frequency resolution at a detector 2105 as mentioned above, information on a structure at a particular position in the direction of the depth of the measuring target can be visualized. As a result, data for one line can be obtained by a single cycle of wavelength sweep, thereby making it possible to construct a tomographic image.

As the light outputted from the light source 2101 is of from 4 to 6 mm or so in coherence length, it is possible to encompass the entire examination range in the direction of the depth of the imaging target. It is, therefore, unnecessary to move the reference mirror, so that the reference mirror 2102 is arranged fixedly at a constant distance. Moreover the reference mirror is not indispensable in this embodiment, a turned optical fiber, which can return back the light, may be set at the distal end of the reference optical path instead of the reference mirror.

Because it is unnecessary to mechanically move the reference mirror as mentioned above, the OCT imaging system making use of a wavelength swept light source, in comparison with the OCT imaging system according to the previously described third embodiment, requires a shorter time for acquiring signals for one line and can raise the frame rate. As opposed to a maximum frame rate of 15 fr/s (i.e., frames/second) in the OCT imaging system according to the third embodiment, the frame rate of the OCT imaging system making use of wavelength swept light source is as high as from 30 to 200 fr/s or so.

In the case of an OCT imaging system irrespective of whether or not it makes use of a wavelength swept light source, blood is supposed to be eliminated upon diagnosis so that absorption of light by blood cell components can be avoided to acquire good images. A low frame rate, therefore, requires the elimination of blood for a longer time. This, however, leads to problems from the clinical standpoint. In the case of an OCT imaging system making use of frequency scanning, images can be acquired over 30 mm or longer in the axial direction of a blood vessel by elimination of blood for several seconds, thereby reducing such clinical problems.

Figure 22:
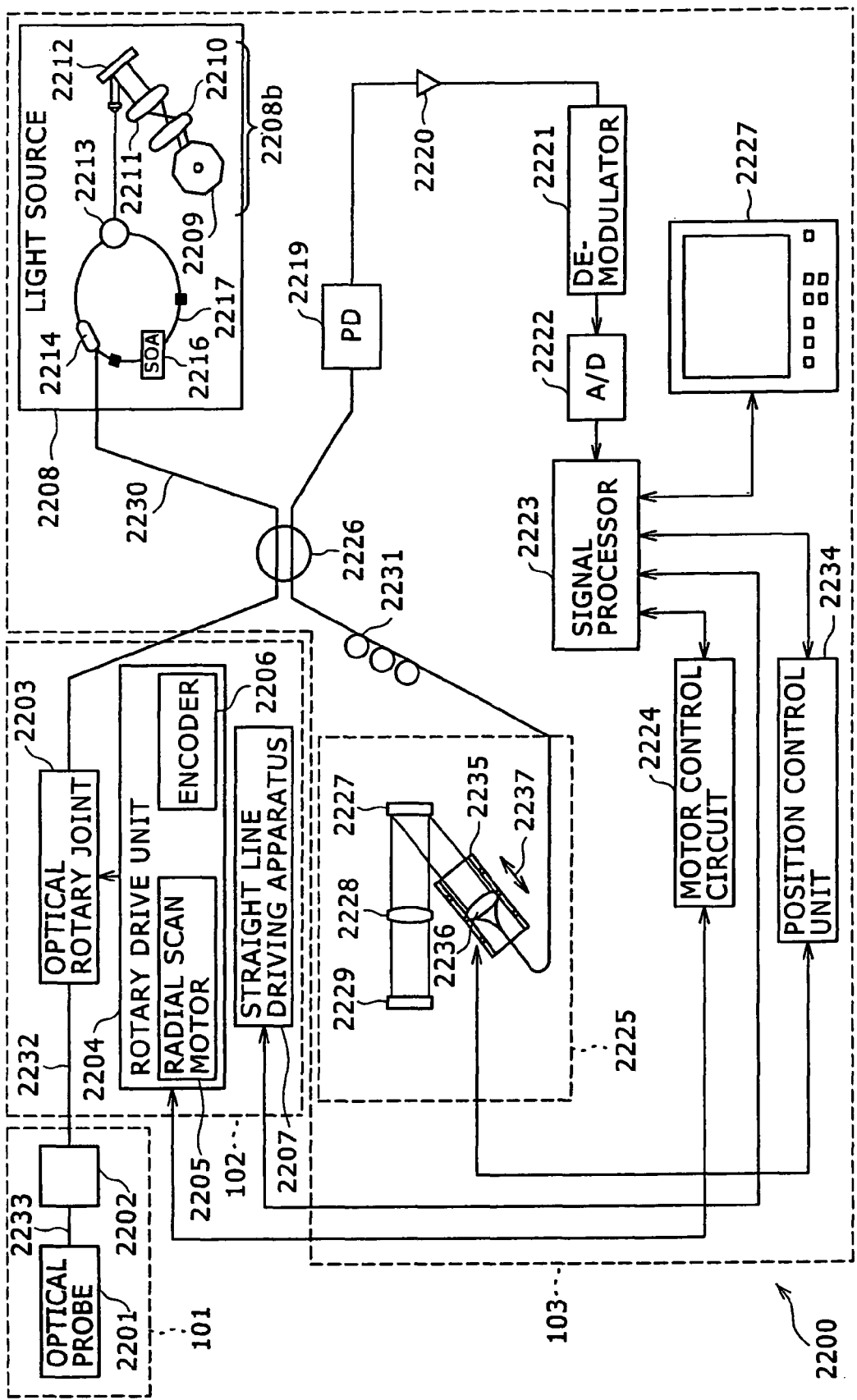
FIG. 22 is a block diagram schematically depicting features of the OCT imaging system making use of a wavelength swept light source.

2. Aspects and Features of OCT Imaging System Making Use of a Wavelength Swept Light Source Aspects and features of the OCT imaging system 2200 making use of a wavelength swept light source are schematically shown in FIG. 22. The description which follows primarily describes differences in the OCT imaging system 2200 making use of a wavelength swept light source relative to the OCT imaging system described above as the third embodiment with reference to FIG. 15.

The OCT imaging system 2200 making use of a wavelength swept light source includes a light source 2208. In the disclosed embodiment, a swept laser is used as the light source 2208. This swept laser 2208 is a kind of extended-cavity laser which includes an optical fiber 2217 and a polygon scanning filter 2208b. The optical fiber 2217 is connected in the form of a ring with a semiconductor optical amplifier (SOA) 2216.

Light outputted from the SOA 2216 advances through the optical fiber 2217 and enters the polygon scanning filter 2208b. Subsequent to wavelength selection through the polygon scanning filter 2208b, the resulting light is amplified at the SOA 2216 and is finally outputted from a coupler 2214.

The polygon scanning filter 2208b selects a wavelength by a combination of a diffraction grating 2212, which separates light into a spectrum, and a polygon mirror 2209. The light, which has been separated into the spectrum by the diffraction grating 2212, is condensed on a facet of the polygon mirror 2209 by two lenses (2210, 2211). As a result, only light of a wavelength crossing at a right angle with the polygon mirror 2209 returns on the same light path and is outputted from the polygon scanning filter 2208b. By rotating the mirror, time sweeping of wavelengths is performed.

As an example of the polygon mirror 2209, a 32-sided polygonal mirror can be used, and its rotational speed can be 50,000 rpm or so. By the unique wavelength sweep system making the combined use of the polygon mirror 2209 and the diffraction grating 2212, high-speed and high-output wavelength sweep is feasible.

The light of the swept laser 2208, which has been outputted from the coupler 2214, impinges on the proximal end of a first single mode fiber 2230 and is transmitted toward its distal end face. At an optical coupler 2226 arranged midway along the first single mode fiber 2230, the first single mode fiber 2230 is optically coupled with a second single mode fiber 2231. Therefore, the light transmitted through the first single mode fiber 2230 is split into two by the optical coupler 2226 and the resulting two beams of light are transmitted further.

On the more distal end side of the first single mode fiber 2230 than the optical coupler 2226, an optical rotary joint 2203 is arranged to connect a non-rotatable block and a rotatable block with each other such that light can be transmitted.

Further, an optical-probe connector 2202 is detachably connected to the distal end of a third single mode fiber 2232 in the optical rotary joint 2203. Via the connector 2202, the light from the light source 2208 is transmitted to a fourth single mode fiber 2233 which is inserted in an optical probe 2201 and is rotationally drivable.

The transmitted light is irradiated from a distal end side of the optical probe 2201 toward a surrounding biotissure of a body cavity while performing radial scanning. A portion of reflected light scattered on a surface or interior of the biotissue is collected by the optical probe 2201, and returns toward the first single mode fiber 2230 through the reverse optical path. A portion of the thus-collected, reflected light is transferred by the optical coupler 2226 to the second single mode fiber 2231 and is introduced into a photodetector (for example, photodiode 2219) from an end of the second single mode fiber 2231. It is to be noted that the rotatable block side of the optical rotary joint 2203 is rotationally driven by a radial scan motor 2205. Further, rotation angles of the radial scan motor 2205 are detected by an encoder 2206. The optical rotary joint 2203 is provided with a linear drive unit 2207 which, based on an instruction from a signal processor 2223, controls movement of the catheter section 101 in the direction of its insertion.

On the more distal end side of the second single mode fiber 2231 than the optical coupler 2226, an optical path length (OPL) varying mechanism 2225 is arranged to finely adjust the optical path length of reference light.

This OPL varying mechanism 2225 is provided with a an OPL varying means for varying the optical path length by a length equivalent to a variation in the length of a new optical probe to absorb the variation when the new optical probe is used as a replacement.

The second single mode fiber 2231 and a collimator lens 2236 are mounted on a single axis stage 2235 movable in the direction of an optical axis of the collimator lens 2236 as indicated by an arrow 2237, thereby forming the OPL varying mechanism.

More specifically, the single axis stage 2235 forms the OPL varying mechanism having a variable OPL range just enough to absorb a variation in the optical path length of a new optical probe when the optical probe 2201 is replaced by the new optical probe. In addition, the single axis stage 2235 is also equipped with a function as an adjustment means for adjusting an offset. Even when the distal end of the optical probe 2201 is not in close contact with a surface of the biotissue, for example, the optical probe can still be set in such a state as interfering from a position on the surface of the biotissue by slightly varying the optical path length with the single axis stage 2235.

The light finely adjusted in optical path length by the OPL varying mechanism 2225 is combined with the light, which has escaped from the side of the first single mode fiber 2230, at the optical coupler 2226 arranged midway along the second single mode fiber 2231, and the combined light is received at the photodiode 2219.

The light received at the photodiode 2219 is photoelectrically converted, amplified by an amplifier 2220, and then inputted into a demodulator 2221. At the demodulator 2221, demodulation processing is performed to extract only the signal portion of the interfered light, and the output of the demodulator 2221 is inputted into an A/D converter 2222.

At the A/D converter 2222, interference light signals are sampled at 180 MHz as much as for 2,048 points to produce digital data (interference light data) for one line. It is to be noted that the setting of the sampling frequency at 180 MHz is attributed to the premise that approximately 90% of the cycle of wavelength sweep (12.5 μsec) be extracted as digital data at 2,048 points when the wavelength sweep repetition frequency is set at 40 kHz. The sampling frequency should be understood, therefore, not to be limited specifically to the above-described value.

The interference light data in line unit, which have been produced at the A/D converter 2222, are inputted into a signal processor 2223. At this signal processor 2223, the interference light data are frequency-resolved by FFT (Fast Fourier Transform) to produce data in the direction of the depth. These data are then coordinate-transformed to construct tomographic images at respective positions in the blood vessel. The tomographic images are then outputted at a predetermined frame rate to an LCD monitor 2227.

The signal processor 2223 is connected with a position control unit 2234. The signal processor 2223 performs control of the position of the single axis stage 2235 via the position control unit 2234. In addition, the signal processor 2223 is also connected with a motor control circuit 2224 to control rotational drive by the radial scan motor 2205.

3. Construction of Catheter Section

The overall construction of the catheter section (i.e., probe) 101 and the construction of the distal end portion of the catheter are similar to those of the distal end and the catheter section in the OCT imaging device described above as the third embodiment with reference to FIG. 16. Thus, a detailed description of the features of the catheter section 101 is not repeated.

4. Features of Signal Processor

Figure 23:
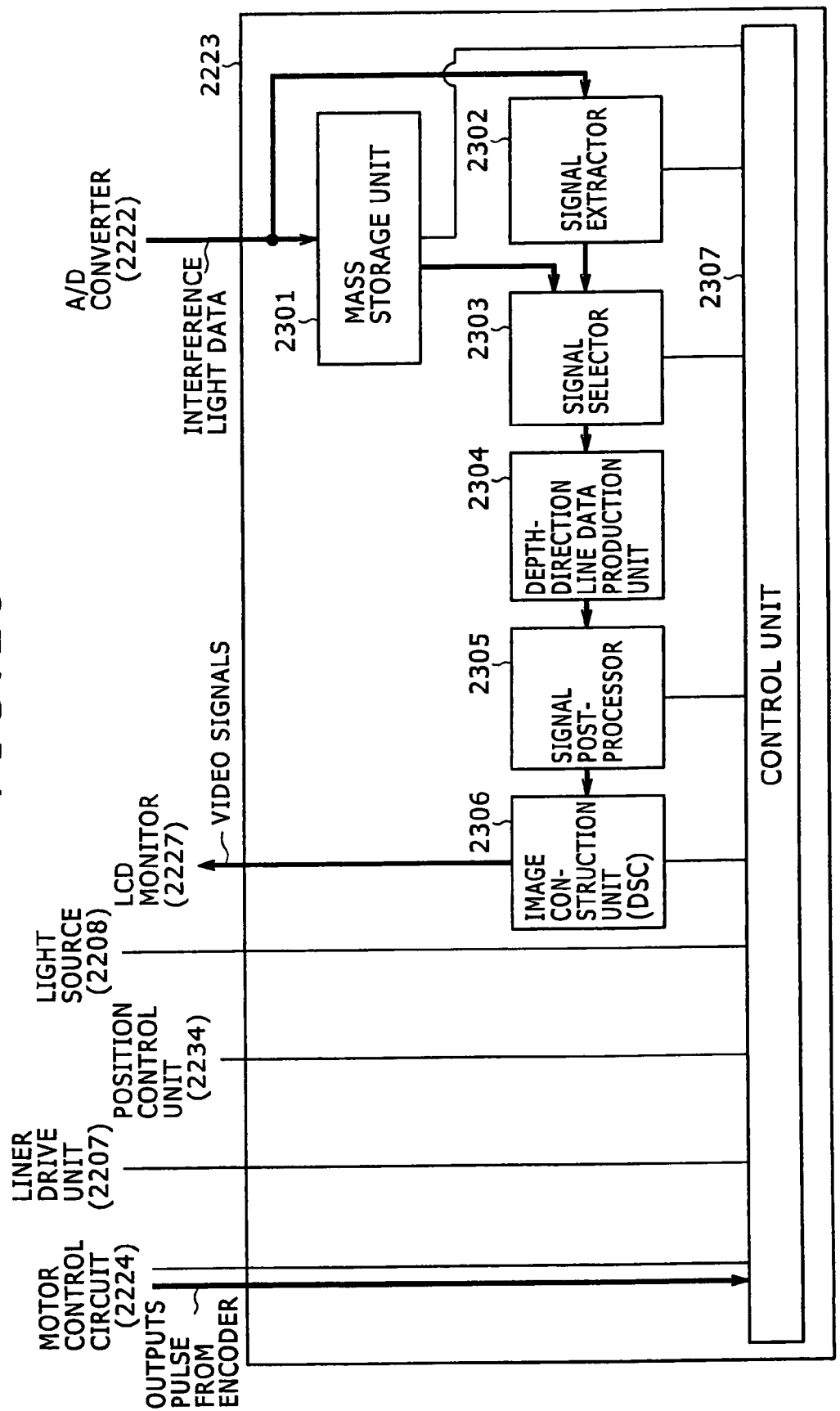
FIG. 23 is a block diagram depicting operational aspects of a signal processor in the OCT imaging system making use of a wavelength swept light source.

Features of the signal processor 2223 in the OCT imaging system 2200 making use of a wavelength swept light source are schematically illustrated in FIG. 23. The signal processor 2223 includes a control unit 2305 which systematically controls the OCT imaging system 2200 making use of a wavelength swept light source in its entirety. The signal processor 2223 also includes mass storage unit 2301 which is composed of a hard disk, semiconductor memory or the like. At the mass storage unit 2301, all interference light data transmitted from the photodiode 2210 via the demodulator 2221 and A/D converter 2222 are successively received and stored in cycle units of wavelength sweep (line units).

The interference light data stored in the mass storage unit 2301 are read in accordance with a frame rate of video signals as needed (based on instructions from the control unit 2307), and are then fed to a signal selector 2303.

The capacity of the mass storage unit 2301 is determined depending on how many frames of data are to be acquired by radial scanning. When a 150-mm blood vessel is subjected to radial scanning at a pitch of 0.5 mm, for example, 300 frames of data are acquired. If each frame consists of 16-bit data of 1,024 lines×2,048 samples, the total data size becomes 1,200 Mbytes. In this case, a semiconductor memory or hard disk of 2 Gbytes or greater can be chosen as the mass storage unit 2301.

A signal extractor 2302 operates to selectively extract predetermined interference light data from the interference light data transmitted from the A/D converter 2222. The signal extractor 2302 can be composed of an FIFO memory with a write inhibit function. In synchronization with each output pulse from the encoder 2206, the write enable/disable status of the FIFO memory is controlled. Only when the FIFO memory is writable, inputted interference light data are written in the FIFO memory.

More specifically, the FIFO memory is made writable in the cycle unit of wavelength sweep (line unit) so that interference light data corresponding to radial scanning for one frame can be constructed. If unnecessary interference light data are inputted, the FIFO memory is write-disabled. Reading from the FIFO memory is performed in synchronization with a timing of subsequent processing, and the thus-read interference light data are outputted to the signal selector 2303. A description of an extraction method of interference light data will be set forth below.

When the signal selector 2303 receives from the control unit 2307 an instruction to the effect that the interference light data stored in the mass storage unit 2301 are to be read, the signal selector 2303 reads the interference light data from the mass storage unit 2301 and transmits them to a depth-direction line data production unit 2304. When the signal selector 2303 receives from the control unit 2307 an instruction for a real-time image display, on the other hand, the signal selector 2303 reads the interference light data extracted at the signal extractor 2302, and transmits them to the depth-direction line data production unit 2304. The depth-direction line data production unit 2304 subjects the interference light data to frequency resolution by FFT (the fast Fourier transform) to produce depth-direction data.

A signal post-processor 2305 performs processing such as frame correlation, gamma correction, contrast adjustment and sharpness filtering on the interference light data transmitted from the depth-direction data production unit 2304, and outputs the resulting data to an image construction unit 2306.

At the image construction unit 2306, streams of interference light data (post-processed depth-direction line data) in wavelength sweep units (line units) are converted into video signals. Based on the video signals, tomographic images to be displayed on the LCD monitor 2227 are constructed.

As a result, when the signal selector 2303 receives from the control unit 2307 an instruction to the effect that the interference light data stored in the mass storage unit 2301 are to be read, the tomographic images formed based on the interference light data stored in the mass storage unit 2301 are displayed on the LCD monitor 2227. When an instruction for a real-time display of images is received, on the other hand, tomographic images formed based on the interference light data extracted at the signal extractor 2302 are displayed on the LCD monitor 2227 corresponding to the radial scanning by the optical probe 2201. In other words, control is effected such that the LCD monitor 2227 performs two types of tomographic image displays, one being a real-time motion display during radial scanning and the other an all data display in slow motion after the radial scanning.

5. Signal Processing During Optical Coherence Tomography Making Use of a Wavelength Swept Light Source

5.1 Outline of Signal Processing

Figure 24A:
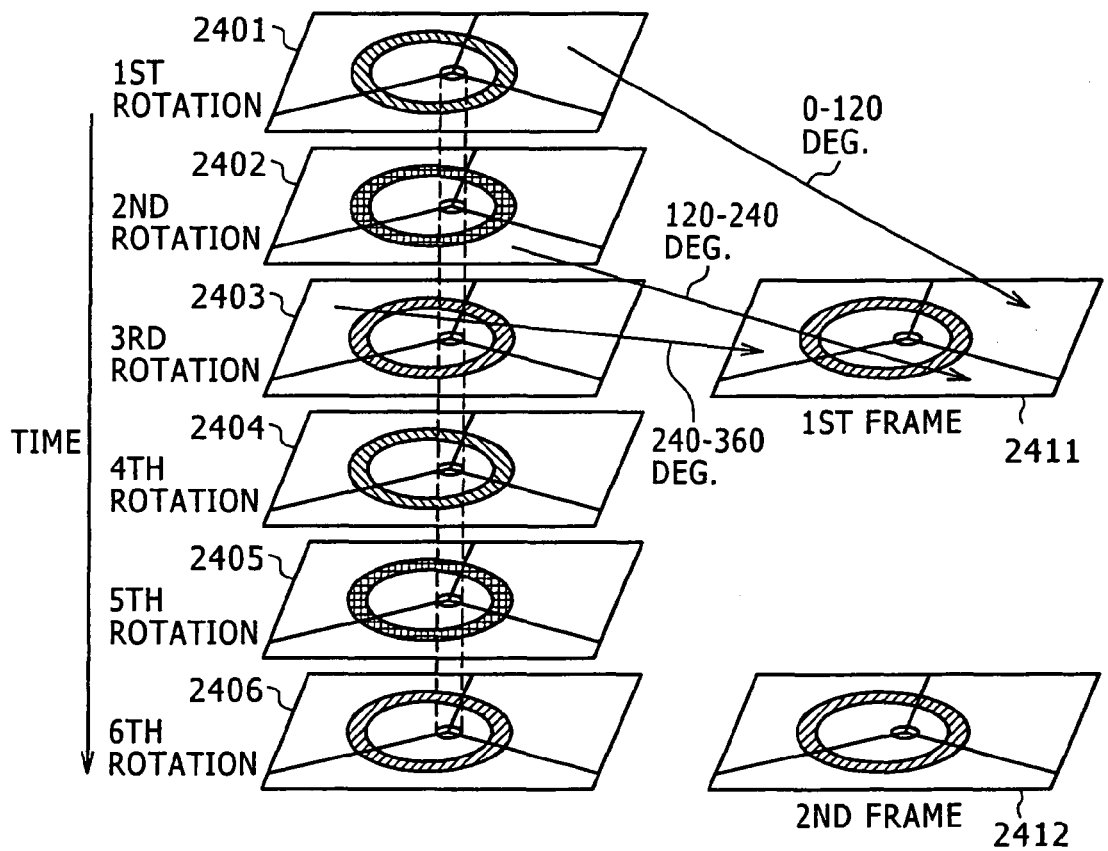
FIGS. 24A and 24B are schematic views illustrating aspects of signal processing in the OCT imaging system making use of a wavelength swept light source.
Figure 24B:
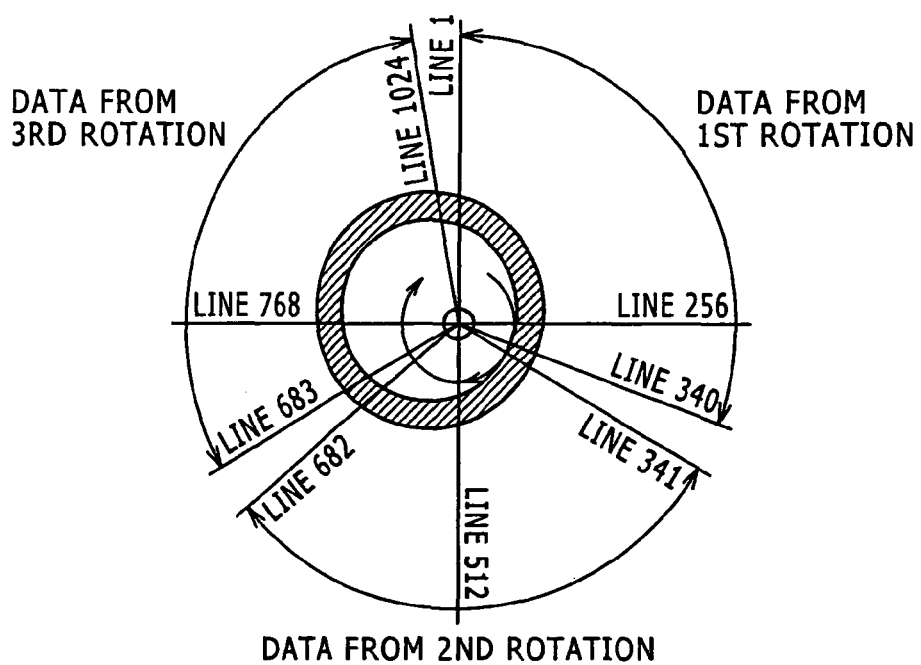

FIGS. 24A and 24B schematically illustrate operational aspects of the signal processing in the OCT imaging system 2200 making use of a wavelength swept light source according to this embodiment during optical coherence tomography. As shown in FIG. 24A, interference light data (1,024 lines) needed to form one tomographic image of a blood vessel are acquired from every rotation of the optical probe 2201 (in the example of FIG. 24A, interference light data (2401-2406) needed to form six tomographic images are acquired from six rotations of the optical probe 2201).

The interference light data acquired from the respective rotations are stored in the mass storage unit 2301 to permit their reproduction after the measurement. In addition, portions of the interference light data acquired from every predetermined number of rotations of the probe are extracted to produce one frame of interference light data, which is displayed in real time. In the example of FIG. 24A, the interference light data for 0 degree to 120 degrees are extracted from the interference light data (2401) acquired from the first rotation, the interference light data for 120 degrees to 240 degrees are extracted from the interference light data (2402) acquired from the second rotation, and the interference light data for 240 degree to 360 degrees are extracted from the interference light data (2403) acquired from the third rotation. These extracted interference light data are combined to produce one frame of interference light data (2411).

FIG. 24B diagrammatically illustrates the breakdown of the one frame of interference light data (2411) produced as described above. As shown, the interference light data (2411) consist of lines 1 to 340 of interference light data from the first rotation, lines 341 to 682 of interference light data from the second rotation, and lines 683 to 1024 of interference light data from the third rotation. The produced interference light data are displayed in real time. Based on the interference light data acquired from the fourth rotation to the six rotation, another one frame of interference light data (2412) are similarly produced and displayed in real time.

As described above, even when the radial scanning by the optical probe 2201 is made faster to increase the number of tomographic images formable per unit time, tomographic images can still be formed at intervals commensurate with the frame rate of video signals by extracting portions of interference light data acquired from every predetermined plural number of rotations and combining them to form one frame of interference light data. As a result, a real-time display becomes feasible.

It is to be noted that in parallel with the above-described extraction of interference light data and the subsequent formation of tomographic images, the interference light data acquired from the respective rotations as mentioned above are stored in the mass storage unit 2301. It is, therefore, possible to display all the interference light data later by reading all the interference light data stored in the mass storage unit 2301. As has been described above, the OCT imaging system 2200 making use of a wavelength swept light source can perform a display of all data and a real-time display of extracted data even when the radial scanning by the optical probe 2201 is made faster.

5.2 Processing at the Individual Units to Realize the Above-described Signal Processing Set forth below is a description of the processing occurring at the individual units in the signal processor 2223 to realize the above-described signal processing. The following description is based on the assumption that the number of lines per rotation is 1,024, though that number can be varied.

5.2.1 Processing at the Control Unit 2307

FIG. 25 is a flow chart showing operational aspects of the processing at the control unit 2307 upon performing a real-time display during intravascular optical coherence tomography making use of a wavelength swept light source. In step S2501, a frame rate of radial scanning and a frame rate of video signals are read. In step S2502, the ratio ($\alpha$) of the frame rate of radial scanning to the frame rate of video signals so read is calculated. In step S2503, the ratio ($\alpha$) calculated in step S2502 is transmitted to the signal extractor 2302.

5.2.2 Processing at the Signal Extractor 2302

Figure 26:
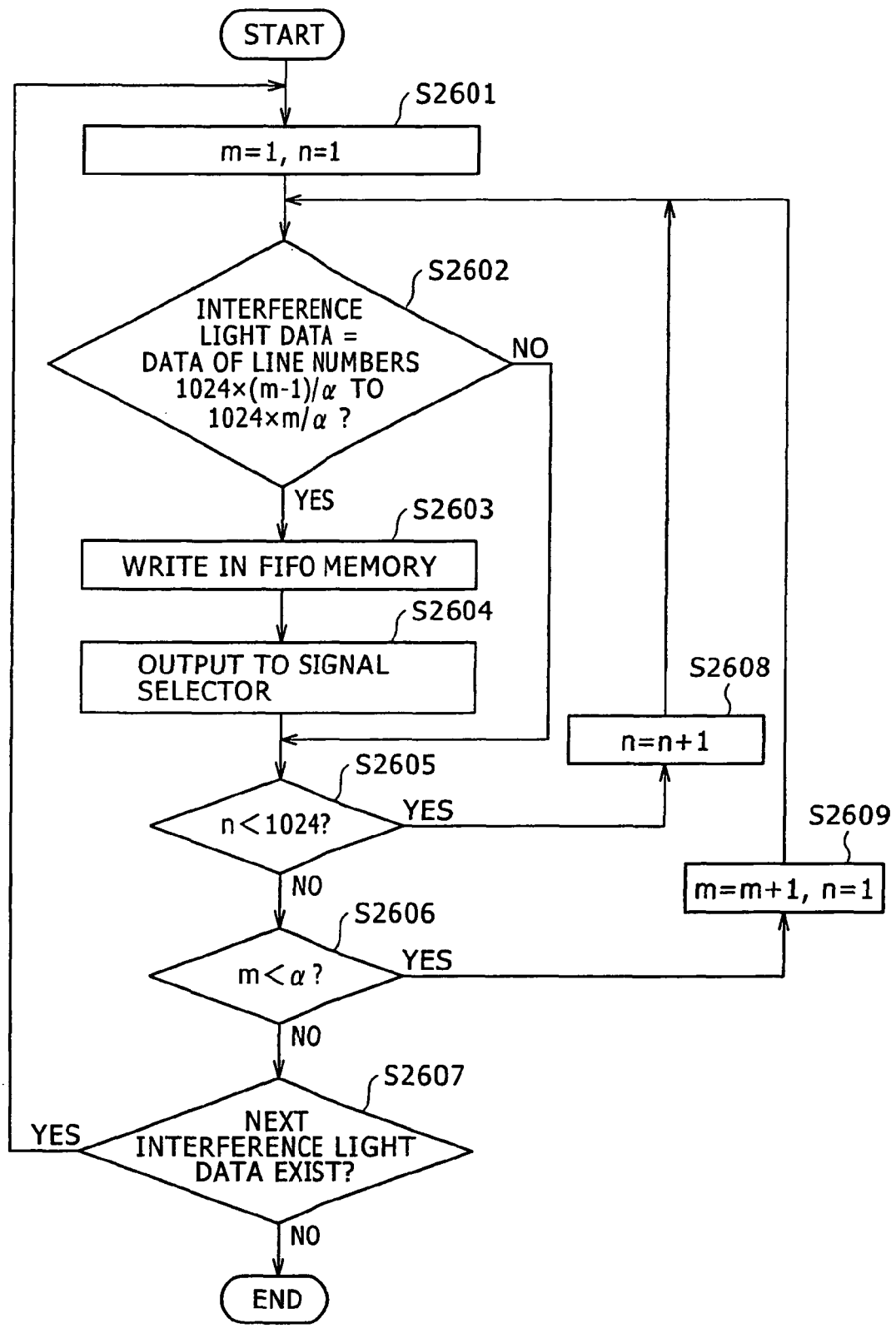
FIG. 26 is a flow chart showing operational aspects of a signal extractor upon conducting a real-time display in optical coherence tomography making use of a wavelength swept light source.

FIG. 26 is a flow chart showing operational aspects of the processing at the signal extractor 2302 upon performing a real-time display during intravascular optical coherence tomography. In step S2601, count values m, n are set at 1, respectively, as initial values. The count value m is a parameter for counting the number of rotations of the optical probe 2201. The count value n, on the other hand, is a parameter for controlling the line number of interference light data.

In step S2602, a determination is made as to whether or not the line number of interference light data (line number=n) transmitted from the A/D converter 2222 satisfies the conditions of the following formulas (Formula 1, Formula 2):

$$1024 \times (m-1)/\alpha \leq n \quad \text{(Formula 1)}$$

$$1024 \times m/\alpha > n \quad \text{(Formula 2)}$$

If the line number is determined to satisfy the conditions of the Formula 1 and Formula 2 in step S2602, the process advances to step S2603, in which the interference light data (line number=n) are written in the FIFO memory. The process then advances to step S2604, in which the interference light data are extracted, and are outputted at a predetermined timing to the signal selector 2303. Subsequently, the process advances to step S2605. In this case, the interference light data will be used for a real-time display.

If the line number is not determined to satisfy the conditions of the Formula 1 and Formula 2 in step S2603, on the other hand, the process advances directly to step S2605. In this case, the interference light data will not be used for a real-time display.

In step S2605, a determination is made as to whether or not the count value n is smaller than 1,024. If the count value n is determined to be smaller than 1,024, the process advances to step S2608 and, after the count value n is incremented, the process returns to step S2602. If the count value n is determined to be equal to 1,024, on the other hand, the process advances to step S2606.

In step S2606, a determination is made as to whether or not the count value m is smaller than $\alpha$. If the count value m is determined to be smaller than $\alpha$, the process advances to step S2609, in which the count value m is incremented and 1 is inputted as the count value n.

If the count value m is determined to be equal to a in step S2606, on the other hand, the process advances to step S2607. In step S2607, a determination is made as to whether or not next interference light data exist. If next interference light data are determined to exist, the process returns to step S2601. If no next interference light data are determined to exist, the processing is ended.

As evident from the above description, the OCT imaging system making use of a wavelength swept light source according to this embodiment can form tomographic images at intervals commensurate with the frame rate of video signals by extracting interference light data on the basis of the ratio of the frame rate of radial screening to the frame rate of video signals. As a result, a real-time display can be performed irrespective of the frame rate of video signals even when the radial scanning by an optical probe is made faster.

In this embodiment, the description has been set forth about the signal processing, which has been described above in the first embodiment, as applied to the OCT imaging system making use of a wavelength swept light source. It is, however, to be noted that the signal processing, which has been described above in the second embodiment, can also be applied to the OCT imaging system making use of a wavelength swept light source by replacing "ultrasound echo data" with "interference light data".

The principles, preferred embodiments and modes of operation have been described in the foregoing specification. However, the invention which is intended to be protected is not to be construed as limited to the particular embodiments disclosed. Further, the embodiments described herein are to be regarded as illustrative rather than restrictive. Variations and changes may be made by others, and equivalents employed, without departing from the spirit of the present invention. Accordingly, it is expressly intended that all such variations, changes and equivalents which fall within the spirit and scope of the present invention as defined in the claims, be embraced thereby.

What is claimed is:

1. An image diagnostic system, comprising:
   a rotary drive unit
   a probe positionable in a body cavity, the probe being connectable to the rotary drive unit and configured to repeatedly transmit signals into a body cavity and receive reflected signals which are reflected by biotissue surrounding the body cavity during radial scanning, the radial scanning comprising rotation of the probe by the rotary drive unit;
   a main control unit configured to produce data based on the reflected signals to construct tomographic images of the body cavity and biotissue; and
   a display unit configured to display the tomographic images of the body cavity and biotissue;
   the main control unit comprising:

an extraction unit configured to extract portions of the produced data based on a frame rate of the display unit;

a first output control unit configured to form, based on the extracted portions of the data extracted by the extraction unit, real time tomographic images of the body cavity and biotissue and to output the real time tomographic images during the radial scanning;

a storage device configured to store the produced data;

a second output control unit configured to form and output, based on the data stored in the storage device, successive tomographic images after the radial scanning; and wherein the main control unit produces an amount of data for each rotation of the probe, and the first control unit forms each of the real time tomographic images by combining a plurality of the portions of the produced data extracted by the extraction unit based on plural tomographic images from several different rotations of the probe so that each real time tomographic image is formed from said amount of data for each rotation of the probe.

2. The image diagnostic system according to claim 1, wherein the probe comprises an ultrasonic transducer configured to transmit and receive ultrasounds, and the data are produced based on waves reflected in the body cavity and acquired through the probe.

3. The image diagnostic system according to claim 1, wherein the probe is connected to a light source adapted to output light, with the probe transmitting and receiving the light, and the data are produced based on interference light between light reflected in the body cavity and acquired through the probe and a reference light split from the light outputted from the light source.

4. An image diagnostic system, comprising:

a probe positionable in a body cavity and configured to repeatedly transmit signals into a body cavity and receive reflected signals which are reflected by biotissue surrounding the body cavity during radial scanning;

a main control unit configured to produce data based on the reflected signals to construct tomographic images of the body cavity and biotissue;

a display unit configured to display the tomographic images of the body cavity and biotissue; and a motor connected to the probe to rotate the probe during the radial scanning at a frame rate faster than a display frame rate of the display unit;

the main control unit comprising:

a storage device configured to store the produced data associated with each rotation of the probe;

an extraction unit configured to extract only a portion of the produced data associated with each rotation of the probe, the extraction unit extracting the produced data associated with a predetermined rotation angle of each rotation of the probe based on a ratio of the frame rate of the probe during radial scanning to the display frame rate;

a first output control unit configured to form real time tomographic images of the body cavity and biotissue based on the data extracted by the extraction unit, and to output the real time tomographic images during the radial scanning; and wherein a single real time tomographic image formed by the first output control unit consists of a plurality of the portions of the produced data extracted by the extraction unit based on plural tomographic images from several different rotations of the probe.

5. The image diagnostic system according to claim 4, wherein the extraction unit extracts only a portion of the produced data before the produced data is stored in the storage device.

6. The image diagnostic system according to claim 5, further comprising a second output control unit configured to form and output, based on the data stored in the storage device, successive tomographic images after the radial scanning.

7. The image diagnostic system according to claim 4, further comprising a second output control unit configured to form and output, based on the data stored in the storage device, successive tomographic images after the radial scanning.

8. An image diagnostic apparatus for controlling a probe, which is adapted to be connected to the image diagnostic apparatus and which repeatedly transmits signals into a body cavity which are reflected by biotissue surrounding the body cavity to perform radial scanning within the body cavity through rotation of the probe, the image diagnostic apparatus comprising:

a main control unit configured to produce data based on the reflected signals and to construct a tomographic image of the body cavity and the biotissue surrounding the body cavity on a basis of the produced data; and a display unit configured to display the tomographic images at a display frame rate;

a rotary drive unit connectable to the probe to rotate the probe;

the main control unit comprising:

an extraction unit configured to extract the produced data associated with predetermined rotation angles which are based on a ratio of a frame rate of the radial scanning to the display frame rate of the display unit;

a first output control unit configured to form, based on the extracted produced data, real time tomographic images of the body cavity and biotissue, and to output the real time tomographic images during the radial scanning;

a storage device configured to store the produced data;

a second output control unit configured to form, based on the produced data stored in the storage device, successive tomographic images and to output the tomographic images after the radial scanning; and wherein the first output control unit produces one frame of data consisting of a plurality of the extracted produced data based on plural frame data from several different rotations of the probe.

9. The image diagnostic apparatus according to claim 8, wherein the probe to which the image diagnostic apparatus is adapted to be connected includes an ultrasonic transducer configured to transmit and receive ultrasounds, and the data are produced based on waves reflected in the body cavity and acquired through the probe.

10. The image diagnostic apparatus according to claim 8, wherein the probe to which the image diagnostic apparatus is adapted to be connected is connected to a light source adapted to output light, with the probe transmitting and receiving the light, and the produced data are based on interference light between light reflected in the body cavity and acquired through the probe and a reference light split from the light outputted from the light source.

11. A method for processing information in an image diagnostic system connected to a probe to produce tomographic images to be displayed on a display unit at a display frame rate, the method comprising:
- transmitting signals from the probe into a body cavity and receiving signals reflected from biotissue surrounding the body cavity during radial scanning of the probe involving rotation of the probe, the probe performing radial scanning at a frame rate;
- producing data based on the received reflected signals;
- extracting portions of the produced data associated with predetermined rotation angles which are based on a ratio of the frame rate of the radial scanning to the display frame rate of the display unit;
- forming real time tomographic images of the body cavity and the biotissue, with each real time image being produced from a plurality of the extracted portions of the produced data, and outputting the real time tomographic images at the frame rate of the display unit;
- storing the produced data; and
- forming tomographic images of the body cavity and the biotissue based on the produced data that has been stored and outputting the tomographic images subsequent to the radial scanning.

12. The method according to claim 11, wherein the extraction of portions of the produced data comprises extracting only a portion of the data produced from one complete rotation of the probe.

13. The method according to claim 11, wherein each rotation of the probe results in the production of an amount of data, and wherein the extraction of portions of the produced data comprises extracting a portion of the data produced from each of plural rotations of the probe, and wherein the forming of the real time tomographic images comprises forming each real time tomographic image based on the extracted portions of the data produced from the plural rotations of the probe.

14. A non-transitory recording medium with a control program stored therein for performing by a computer the method according to claim 11.

15. A method for producing a tomographic image of a body cavity and surrounding biotissue comprising:
- positioning a probe in a body cavity;
- transmitting signals from the probe into the body cavity and receiving signals reflected from the biotissue surrounding the body cavity while rotating the probe at a frame rate to perform radial scanning;
- producing data as produced data based on the received reflected signals;
- extracting only a portion of the produced data associated with predetermined rotation angles of each rotation of the probe;
- forming real time tomographic images of the body cavity and biotissue based on the extracted data;
- displaying the real time tomographic images during the radial scanning at a frame rate less than the frame rate of the probe during the radial scanning, the real time tomographic images being displayed at a display frame rate; and
- the extracting of only a portion of the produced data comprising extracting only a portion of the produced data associated with the predetermined rotation angles which are based on a ratio of the frame rate at which the probe is rotating and the display frame rate at which the tomographic images are displayed, and each real time tomographic image consists of a plurality of the portions of the produced data from different rotations.

16. The method according to claim 15, further comprising storing the produced data as stored produced data, and forming successive tomographic images subsequent to radial scanning using the stored produced data.

17. The method according to claim 15, wherein the probe transmits and receives ultrasounds.

18. The method according to claim 15, wherein the probe transmits and receives light outputted from a light source, and the produced data are produced based on interference light between light reflected in the body cavity and acquired through the probe and a reference light split from the light outputted from the light source.

* * * * *